(12) United States Patent
Türk et al.

(10) Patent No.: US 9,066,891 B2
(45) Date of Patent: Jun. 30, 2015

(54) DENDRITIC POLYETHER-POLYURETHANE THICKENERS

(75) Inventors: Holger Türk, Mannheim (DE); Volker Wendel, Seeheim-Jugenheim (DE); Anna Cristadoro, Heppenheim (DE); Daniel Stadler, Mannheim (DE); Markus Buchmann, Freinsheim (DE)

(73) Assignee: BASF SE, Lundwigshafen (DE)

( * ) Notice: Subject to any disclaimer, the term of this patent is extended or adjusted under 35 U.S.C. 154(b) by 327 days.

(21) Appl. No.: 13/344,676

(22) Filed: Jan. 6, 2012

(65) Prior Publication Data

US 2012/0190756 A1    Jul. 26, 2012

Related U.S. Application Data

(60) Provisional application No. 61/434,457, filed on Jan. 20, 2011.

(51) Int. Cl.
| | |
|---|---|
| C08G 18/00 | (2006.01) |
| A61K 8/87 | (2006.01) |
| C08G 18/48 | (2006.01) |
| A61Q 19/00 | (2006.01) |
| C08G 83/00 | (2006.01) |
| C08G 18/73 | (2006.01) |
| C08G 18/75 | (2006.01) |
| C08G 18/10 | (2006.01) |
| C08L 101/00 | (2006.01) |
| C08G 18/28 | (2006.01) |
| A61Q 5/12 | (2006.01) |
| A61Q 9/04 | (2006.01) |
| A61Q 15/00 | (2006.01) |
| A61Q 17/04 | (2006.01) |

(52) U.S. Cl.
CPC .............. *A61K 8/87* (2013.01); *C08G 18/283* (2013.01); *C08G 18/2835* (2013.01); *C08G 18/4829* (2013.01); *A61K 2800/48* (2013.01); *A61K 2800/544* (2013.01); *A61Q 5/12* (2013.01); *A61Q 9/04* (2013.01); *A61Q 15/00* (2013.01); *A61Q 17/04* (2013.01); *A61Q 19/00* (2013.01); *C08G 18/4825* (2013.01); *C08G 18/4833* (2013.01); *C08G 83/005* (2013.01); *C08G 18/73* (2013.01); *C08G 18/755* (2013.01); *C08G 18/10* (2013.01); *C08G 18/284* (2013.01); *C08L 101/005* (2013.01)

(58) Field of Classification Search
CPC ............. C08G 18/283; C08G 18/2835; C08G 18/4829
USPC .................................................... 528/49, 77
See application file for complete search history.

(56) References Cited

U.S. PATENT DOCUMENTS

| | | | |
|---|---|---|---|
| 3,932,532 A | 1/1976 | Hunter et al. | |
| 4,079,028 A | 3/1978 | Emmons et al. | |
| 4,155,892 A * | 5/1979 | Emmons et al. ............... | 524/507 |
| 5,612,408 A | 3/1997 | Konig et al. | |
| 5,753,731 A * | 5/1998 | Yoshioka et al. ............. | 524/198 |
| 2005/0187342 A1 | 8/2005 | Schieferstein et al. | |
| 2008/0108775 A1 | 5/2008 | Schieferstein et al. | |
| 2009/0082483 A1 | 3/2009 | Petrovic et al. | |
| 2009/0286940 A1 | 11/2009 | Frings et al. | |
| 2010/0324261 A1 * | 12/2010 | Muelhaupt et al. ........... | 528/425 |
| 2011/0166291 A1 | 7/2011 | Turk et al. | |
| 2012/0082629 A1 * | 4/2012 | Turk et al. ....................... | 424/54 |

FOREIGN PATENT DOCUMENTS

| | | |
|---|---|---|
| DE | 19947631 | 6/2000 |
| DE | 10211664 | 10/2003 |
| DE | 10307172 | 5/2005 |
| EP | 0725097 | 8/1996 |
| EP | 0761780 | 3/1997 |
| EP | 0978522 | 2/2000 |
| EP | 1566393 | 8/2005 |
| EP | 1584331 | 10/2005 |
| WO | WO-00/56802 | 9/2000 |
| WO | WO-2004/074346 | 9/2004 |
| WO | WO-2006/002813 | 1/2006 |
| WO | WO-2009/101141 | 8/2009 |
| WO | WO-2009/135856 | 11/2009 |

OTHER PUBLICATIONS

Chen, Yu et al., "Synthesis of Multihydroxyl Branched Polyethers by Cationic Copolymerization of 3,3-Bis(hydroxymethyl)oxetane and 3-Ethyl-3-(hydrocymethyl)oxetane", *Chem. Journal Poly. Sci. Part A: Polym. Chem.*, vol. 40 2002, pp. 1991-2002.
Flory, Paul J. et al., "Molecular Size Distribution in Three Dimensional Polymers. VI. Branched Polymers Containing A-R-Bf-1 Type Units", *Journal. Am. Chem. Soc.* vol. 74 1952, pp. 2718-2723.
Frey, Holger et al., "Controlling the Growth of Polymer Trees: Concepts and Perspectives for Hyperbranched Polymers", *Chem. Eur. J.*, vol. 6, Nr. 14 2000, pp. 2499-2506.
Frey, H. et al., "Degree of branching in hyperbranched polymers", *Acta Polym.*, vol. 48 1997, pp. 30-35.
Haag, Rainer et al., "An Approach to Glycerol Dendrimers and Pseudo-Dendritic Polyglycerols", *J. Am. Chem. Soc.*, vol. 122 2000, pp. 2954-2955.
Malmstrom, Eva et al., "Hyperbranched Polymers: A Review", *Journal of Molecular Science* Rev. Macromol. Chem. Phys.; C (37)3 1997, pp. 555-579.

\* cited by examiner

*Primary Examiner* — Michael L Leonard
(74) *Attorney, Agent, or Firm* — Servilla Whitney LLC

(57) ABSTRACT

Described are associative polyether-polyurethane thickeners into which dendritic polyetherpolyols have been polymerized-in. Also described is the preparation of these thickeners, and the use thereof, in particular, in cosmetic preparations.

11 Claims, No Drawings

DENDRITIC POLYETHER-POLYURETHANE THICKENERS

CROSS-REFERENCE TO RELATED APPLICATIONS

This application claims the benefit of priority of U.S. Provisional Application Ser. No. 61/434,457, filed on Jan. 20, 2011, which is incorporated herein by reference in its entirety.

TECHNICAL FIELD

The present invention relates to associative polyether-polyurethane thickeners into which dendritic polyetherpolyols have been polymerized-in, to the preparation of these thickeners, and to the use thereof, in particular in cosmetic preparations.

BACKGROUND

Associative thickeners based on polyurethane belong to the prior art. They are described in detail, for example, in U.S. Pat. Nos. 4,079,028 and in 4,155,892.

The "star-shaped products" (group B) and "complex polymers" (group C) described in U.S. Pat. No. 4,079,028 comprise polyurethanes into which polyhydric alcohols have been polymerized-in. These polyhydric alcohols are low molecular weight compounds such as, for example, trimethylolpropane, pentaerythritol, sorbitol, erythritol, mannitol or dipentaerythritol.

EP 1566393 (Cognis) describes thickeners based on an aqueous preparation of nonionic, water-dispersible or water-soluble polyurethanes which can be prepared by reacting (a) one or more polyfunctional isocyanates with (b) one or more polyetherpolyols, (c) one or more monofunctional alcohols and (d) if desired one or more polyfunctional alcohols, where the compounds (d) comprise no further functional groups apart from the OH groups. The polyfunctional alcohols (d) comprise at least predominantly trifunctional alcohols, such as, for example, glycerol or preferably trimethylolpropane.

EP 1765900 (Cognis) describes thickeners based on an aqueous preparation of nonionic, water-dispersible or water-soluble polyurethanes with a specific structure. The particular structure of these polymers is achieved by the presence of allophanate bonds, which are produced by using an excess of isocyanate. As component (a), it is possible to use hydrophilic polyols with at least 2 OH groups, which may additionally comprise ether groups.

EP 1584331 A1 (Shiseido) describes polyurethane thickeners for cosmetic preparations. The polyurethanes may also be branched. The parent polyols and the alkoxylated derivatives thereof are described in paragraphs [38] and [39].

EP 725097 A1 (Bayer) also describes thickeners based on polyurethanes. Branches can optionally be introduced into the polyurethanes by virtue of component a4). a4) is 3- to 6-hydric alcohols in the molecular weight range 92 to 600, preferably 92 to 400 and particularly preferably 92 to 200, such as, for example, glycerol, trimethylolpropane, pentaerythritol and/or sorbitol. If used at all, preference is given to using glycerol or trimethylolpropane.

EP 978522 (National Starch) describes branched polyurethane thickeners with the following formula

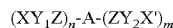

Herein, A is a hydrophilic polyol and preferably selected from trimethylolpropane, [2-ethyl-2-(hydroxymethyl)-1,3-propanediol], pentaerythritol, glycerol and sorbitol.

US 2009/0286940 A1 (DIC Corp.) describes the preparation of hyperbranched polyetherpolyols by ring-opening polymerization of hydroxyalkyl oxetanes and monofunctional epoxides, and also polyurethanes based on these hyperbranched polyetherpolyols.

US 2009/0082483 A1 describes polyurethane foams based on the reaction products of polyisocyanates and polyglycerol, which is hydrophobically modified prior to the urethanization by means of transesterification with naturally occurring polyol esters.

WO 2009/101141 A1 describes a process for the preparation of dendritic polyetherols in which at least one tri- or higher-functional alcohol and optionally further di- and/or monofunctional alcohols and/or modifying reagents are reacted with the help of acidic catalysts. Furthermore, the use of these polyetherols as possible building blocks for the preparation of polyaddition or polycondensation polymers is described.

DE 10211664 A1 describes the synthesis of hyperbranched polyglycerols by ring-opening polymerization of glycidol.

SUMMARY

Embodiments of the present invention are directed to a polymer. The polymer comprises, in polymerized-in form, (a) at least one polyisocyanate, (b) at least one alcohol of the general formula I, (c) at least one dendritic polyetherpolyol, (d) optionally, at least one compound, different from (b) and (c) with a molecular weight of at least 300 g/mol, comprising (i) at least two OH groups, and (ii) at least two groups selected from ether and ester groups, and (e) optionally, further compounds within the region of 1 to 9 groups reactive toward isocyanate groups per molecule.

In one or more embodiments, the at least one dendritic polyether polyol (c) is obtainable by condensation of at least one tri- or higher-functional alcohol and, optionally, further di- and/or monofunctional alcohols and/or modifying agents with the help of acidic catalyst.

In one or more embodiments, the at least one dendritic polyetherpolyol (c) is the condensation product of, on average, at least 3 di-, tri-, or higher-functional alcohols. The at least one dendritic polyetherpolyol (c) can have a number-average molecule weight $M_n$ of at least 300 g/mol.

In a specific embodiment, the at least one dendritic polyetherpolyol (c) comprises polyglycerol.

In one or more embodiments, the polymer is water-soluble or water-dispersible.

In one or more embodiments, in the region of 5 to 95% of the OH groups present in the at least one dendritic polyetherpolyol (c) before the polymerization are also present as OH groups after the polymerization.

In one or more embodiments, the at least one alcohol of the general formula I (b) comprises a $C_{12}$-$C_{30}$ alcohol which has been ethoxylated with 3 to 100 mol of ethylene oxide per mole.

In one or more embodiments, (d) comprises a polyethylene glycol with a molecular with $M_n$ in the range from 1500 to 12,000 g/mol.

Other embodiments of the present invention are directed to a polymer obtainable by reacting at least some of the free OH groups of a polymer according to the invention with compounds reactive toward OH groups.

Further embodiments of the present invention are directed to a process for the preparation of a polymer according to the invention. The process comprises the steps of (1) introducing at least one compound, different from (b) and (c) with a molecular weight of at least 300 g/mol, comprising (i) at least two OH groups, and (ii) at least two groups selected from ether and ester groups (d) as initial charge; (2) adding at least one polyisocyanate (a); (3) starting the addition of at least one alcohol of the general formula I (b) provided that the NCO value is in the range from 80% to 5% of the starting value; and (4) starting the addition of at least one dendritic polyetherpolyol (c) provided that the NCO value is in the range from 50 to 5% of the starting value.

Still further embodiments of the present invention are directed to a process for the preparation of a polymer according to the invention. The process comprises the steps of (1) introducing at least one alcohol of the general formula I (b) as initial charge; (2) adding at least one polyisocyanate (a); and (3) starting the addition of at least one dendritic polyetherpolyol (c) provided that the NCO value is in the range from 80% to 5% of the starting value.

In one or more embodiments of the present invention, the polymer according to the invention can be used as a thickener for aqueous preparations.

Other embodiments of the present invention are directed to a cosmetic preparation comprising at least one polymer according to the invention.

DETAILED DESCRIPTION

Before describing several exemplary embodiments of the invention, it is to be understood that the invention is not limited to the details of construction or process steps set forth in the following description. The invention is capable of other embodiments and of being practice or being carried out in various ways.

Provided are thickeners suitable for cosmetic applications which are distinguishable from the known thickeners by virtue of
A) ability to achieve higher viscosities compared to conventional associative thickeners;
B) increase in the solubility in water;
C) option of adapting the molecular structure to different requirements.

The present invention provides polymers comprising, in polymerized-in form,
a) at least one polyisocyanate
b) at least one alcohol of the general formula I

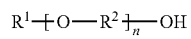 (I)

where
$R^1$ is selected from $C_6$-$C_{40}$-alkyl, $C_6$-$C_{40}$-alkenyl, $C_3$-$C_{10}$-cycloalkyl, $C_6$-$C_{30}$-aryl, $C_7$-$C_{40}$-arylalkyl;
$R^2$ is selected from $C_2$-$C_{10}$-alkylene, $C_6$-$C_{10}$-arylene, $C_7$-$C_{10}$-arylalkylene;
n is 0 to 200,
c) at least one dendritic polyetherpolyol,
d) optionally at least one compound, different from b) and c), with a molecular weight $M_n$ of at least 300 g/mol, comprising
  i. at least two OH groups and
  ii. at least two groups selected from ether groups and ester groups,
e) optionally further compounds within the region of 1 to 9 groups reactive toward isocyanate groups per molecule.

In a specific embodiment, the polymer according to the invention is water-soluble or water-dispersible.

Within the context of this invention, "water-soluble" means that at least 1 gram, preferably at least 10 grams, of the substance referred to as water-soluble, i.e. for example the polymer according to the invention, dissolve in 1 liter of demineralized water to give a solution that is clear to the human eye.

Within the context of this invention, "water-dispersible" means that at least 1 gram, preferably at least 10 grams, of the substance referred to as water-dispersible, i.e. for example the polymer according to the invention, are dispersible in 1 liter of demineralized water without sedimentation with a maximum average particle size of 1 μm.

In a specific embodiment, the polymer according to the invention is uncrosslinked.

Within the context of this invention, "uncrosslinked" means that a degree of crosslinking of less than 15% by weight, preferably of less than 10% by weight, and in particular less than 5% by weight, determined via the insoluble fraction of the polymer, is present. The insoluble fraction of the polymers is determined by extraction for four hours with the same solvent as is used for the gel permeation chromatography for determining the molecular weight distribution of the polymers, i.e. tetrahydrofuran, dimethylacetamide or hexafluorisopropanol, depending on in which solvent the polymer is more soluble, in a Soxhlet apparatus and, after drying the residue to constant weight, weighing the remaining residue.

In a specific embodiment, the polymer according to the invention is water-soluble or water-dispersible and uncrosslinked.

a) Polyisocyanate

According to the present invention, polyisocyanates are compounds with at least two to at most four isocyanate groups per molecule. Suitable polyisocyanates comprise, on average, 2 (diisocyanates) to at most 4 NCO groups per molecule. In a specific embodiment, the polyisocyanate (a) is a diisocyanate.

For example, suitable isocyanates which may be mentioned are 1,5-naphthylene diisocyanate, 4,4'-diphenylmethane diisocyanate (MDI), xylylene diisocyanate (XDI), tetramethylxylene diisocyanate (TMXDI), 4,4'-diphenyldimethylmethane diisocyanate, di- and tetraalkyldiphenylmethane diisocyanate, 4,4-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1-isocyanatomethyl-S-isocyanato-1-trimethyl-cyclohexane, 4,4'-diisocyanatophenylperfluorethane, tetramethoxybutane 1,4-diisocyanate, butane 1,4-diisocyanate, hexane 1,6-diisocyanate (HDI), isophorone diisocyanate (IPDI), dicyclohexylmethane diisocyanate, cyclohexane 1,4-diisocyanate, ethylene diisocyanate, bis-isocyanatoethyl phthalate.

In a specific embodiment, the polymers according to the invention comprise polymerized-in (condensed-in) cycloaliphatic or aliphatic diisocyanate radicals, particularly preferably aliphatic diisocyanate radicals.

Condensed-in aliphatic diisocyanates which may be mentioned by way of example are: 1,4-butylene diisocyanate, 1,12-dodecamethylene diisocyanate, 1,10-decamethylene diisocyanate, 2-butyl-2-ethylpentamethylene diisocyanate, 2,4,4- or 2,2,4-trimethylhexamethylene diisocyanate and in particular hexamethylene diisocyanate (hexane 1,6-diisocyanate, HDI).

Condensed-in cycloaliphatic diisocyanates which may be mentioned by way of example are: isophorone diisocyanate (IPDI), 2-isocyanatopropylcyclohexyl isocyanate, 4-methylcyclohexane1,3-diisocyanate (H-TDI) and 1,3-bis(isocyanatomethyl)cyclohexane. Also so-called $H_{12}$-MDI or diisocyanates referred to as "saturated MDI", such as e.g. 4,4'-methylenebis(cyclohexyl isocyanate) (alternatively also called dicyclohexylmethane 4,4'-diisocyanate) or 2,4'-methylenebis(cyclohexyl) diisocyanate may also be present as radicals in the polyurethanes according to the invention.

In one or more embodiments, a) is or comprises hexamethylene diisocyanate.

In a specific embodiment, a) is or comprises isophorone diisocyanate. It is, of course, also possible to use mixtures of polyisocyanates as a).

b) Alcohol of the General Formula I

Alcohols are of the general formula I

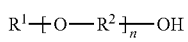  (I)

where
$R^1$ is selected from $C_6$-$C_{40}$-alkyl, $C_6$-$C_{40}$-alkenyl, $C_3$-$C_{10}$-cycloalkyl, $C_6$-$C_{30}$-aryl, $C_7$-$C_{40}$-arylalkyl;
$R^2$ is selected from $C_2$-$C_{10}$-alkylene, $C_6$-$C_{10}$-arylene, $C_7$-$C_{10}$-arylalkylene;
n is 0 to 200.

In one or more embodiments, $R^1$ is $C_6$-$C_{40}$-alkyl. In a specific embodiment, this is a $C_6$-$C_{30}$-alkyl radical, particularly preferably a $C_8$-$C_{30}$-alkyl radical and very particularly preferably a $C_{12}$-$C_{30}$-alkyl radical.

$R^1$ is, for example, selected from radicals of linear or branched alkanes such as hexane, heptane, octane, 2-ethylhexane, nonane, decane, undecane, dodecane, tridecane, isotridecane, tetradecane, pentadecane, hexadecane, heptadecane, octadecane, nonadecane, eicosane, henicosane, docosane, tricosane, isotricosane, tetracosane, pentacosane, hexacosane, heptacosane, octacosane, nonacosane, triacontane, 2-octyldodecane, 2-dodecylhexadecane, 2-tetradecyloctadecane, 2-decyltetradecane, or monomethyl-branched isooctadecane.

In one or more embodiments, $R^1$ is $C_6$-$C_{40}$-alkenyl. Suitable $C_6$-$C_{40}$-alkenyl radicals may be straight-chain or branched. These are preferably predominantly linear alkenyl radicals, as also occur in natural or synthetic fatty acids and fatty alcohols and also oxo alcohols, which are mono-, di- or polyunsaturated. These include e.g. n-hexenyl, n-heptenyl, n-octenyl, n-nonenyl, n-decenyl, n-undecenyl, n-dodecenyl, n-tridecenyl, n-tetradecenyl, n-pentadecenyl, n-hexadecenyl, n-heptadecenyl, n-octadecenyl, n-nonadecenyl.

In one or more embodiments, $R^1$ is $C_3$-$C_{13}$-cycloalkyl. Cycloalkyl is preferably cyclopentyl, cyclohexyl, cycloheptyl or cyclooctyl.

In one or more embodiments, $R^1$ is $C_6$-$C_{30}$-aryl. Aryl comprises unsubstituted and substituted aryl groups and is preferably phenyl, tolyl, xylyl, mesityl, naphthyl, fluorenyl, anthracenyl, phenanthrenyl, naphthacenyl and in particular phenyl, tolyl, xylyl or mesityl.

In one or more embodiments, $R^1$ is $C_7$-$C_{40}$-arylalkyl. Arylalkyl stands for groups which comprise both alkyl and aryl radicals, these arylalkyl groups being linked to the compound carrying them either via the aryl radical or via the alkyl radical. For example, $R^1$ may be an arylalkyl radical, as described in EP 761780 A2, p. 4, l 53-55.

In a specific embodiment, $R^2$ in the general formula (I) is selected from —$CH_2$—$CH_2$—, —$CH(CH_3)$—$CH_2$— and mixtures thereof, particularly preferably —$CH_2$—$CH_2$—.

In a specific embodiment, in the general formula (I), n is selected from the range 2 to 150.

In one or more embodiments, $R^1$ is a branched alkyl radical. The side chains of such branched alkyl radicals are likewise alkyl radicals or alkenyl radicals, particularly preferably alkyl radicals, in particular unbranched alkyl radicals.

In one or more embodiments, the side chains of the branched alkyl radicals $R^1$ have a chain length of at most 6, preferably of at most 4, carbon atoms.

In one or more embodiments, the branches are considerably shorter than the main chain.

In one or more embodiments, each branch of $R^1$ has a chain length which corresponds to at most half of the chain length of the main chain of $R^1$. In one or more embodiments, the branches are considerably shorter than the main chain. In a specific embodiment, the branched $R^1$ are iso- and/or neoalkyl radicals. In a specific embodiment, the branched alkyl radicals $R^1$ used are radicals of isoalkanes. Particular preference is given to a $C_{13}$-alkyl radical, in particular an iso-$C_{13}$-alkyl radical.

In another embodiment, $R^1$ comprises branched alkyl radicals, the side chains of which have a chain length of at least 4, preferably of at least 6, carbon atoms.

In general, b) may also be a mixture of different alcohols.

In a specific embodiment of the invention, at least one alcohol b) is selected from alkoxylated alcohols. Preferred alkoxylated alcohols are ethoxylated alcohols ($R^2$=—$CH_2$—$CH_2$—), propoxylated alcohols ($R^2$=—$CH(CH_3)$—$CH_2$—) and alcohols which are both ethoxylated and propoxylated. In this connection, the ethylene oxide units and propylene oxide units may be in random or blockwise distribution.

Suitable alcohols b) are, for example, the alkoxylated, preferably ethoxylated
  linear alcohols from natural sources or from the Ziegler build-up reaction of ethylene in the presence of aluminum alkyl catalysts. Examples of suitable linear alcohols are linear $C_6$-$C_{30}$-alcohols, in particular $C_{12}$-$C_{30}$-alcohols. Particularly preferred alcohols which may be mentioned are: n-dodecanol, n-tetradecanol, n-hexadecanol, n-octadecanol, n-eicosanol, n-docosanol, n-tetracosanol, n-hexacosanol, n-octacosanol, and/or n-tricontanol, and also mixtures of the aforementioned alcohols, for example NAFOL® grades such as NAFOL®22+ (Sasol).
  oxo alcohols such as, for example, isoheptanol, isooctanol, isononanol, isodecanol, isoundecanol, isotridecanol (for example Exxal® grades 7, 8, 9, 10, 11, 13).
  alcohols which are branched in the 2 position; these are the Guerbet alcohols known to the person skilled in the art which are accessible by dimerizing primary alcohols via the so-called Guerbet reaction. Particularly preferred alcohols which may be mentioned here are: Isofol®12 (Sasol), Rilanit®G16 (BASF SE).
  alcohols which are obtained by the Friedel-Crafts alkylation with oligomerized olefins and which then comprise an aromatic ring as well as a saturated hydrocarbon radical. Particularly preferred alcohols which may be mentioned here are: i-octylphenol and i-nonylphenol.
  alcohols of the general formula (4) of EP 761780 A2, p. 4

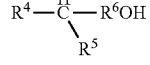

or alcohols of the general formula (5) of EP 761780 A2, p. 4

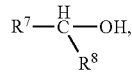

where
$R^4$, $R^5$, $R^7$ and $R^8$, independently of one another, have the meaning described in EP 761780 A2, p. 4, lines 45 to 58; preferably, $R^4$, $R^5$, $R^7$ and $R^8$, independently of one another, are alkyl radicals with at least 4 carbon atoms and the total number of carbon atoms in the alcohols is at most 30, $R^6$ is an alkylene radical such as, for example —$CH_2$—, —$CH_2$—$CH_2$—, —$CH_2$—$CH(CH_3)$—; for example, mention may be made here of 2-decyl-1-tetradecanol as a suitable alcohol.

In one or more embodiments, at least one alcohol b) is a mixture of ethoxylated linear $C_{16}$-$C_{18}$-fatty alcohols.

In one or more embodiments, at least one alcohol b) is a linear, nonionic compound of the structural formula $RO(CH_2CH_2O)_xH$, where R is a linear $C_{16}$-$C_{18}$-alkyl radical, and x is selected from 3, 5, 7, 8, 11, 13, 18, 25 or 80, preferably x=11. Such an ethoxylated, linear fatty alcohol is commercially available for example as Lutensol®AT11 (BASF SE).

In one or more embodiments, at least one alcohol b) is selected from compounds of the structural formula $RO(CH_2CH_2O)_xH$, where R is a linear $C_8$-$C_{30}$-alkyl radical, preferably linear $C_{16}$-$C_{18}$-alkyl radical, and x is 2 to 30.

In one or more embodiments, particularly if no compound d) is polymerized-in, at least one alcohol b) is selected from compounds of the structural formula $RO(CH_2CH_2O)_xH$, where R is a linear $C_8$-$C_{30}$-alkyl radical, preferably linear $C_{16}$-$C_{18}$-alkyl radical and x is 30 to 150.

In one or more embodiments, b) comprises a $C_{12}$-$C_{30}$-alcohol which has been ethoxylated with 3 to 100 mol of ethylene oxide per mole.

In one or more embodiments, b) is selected from mixtures of ethoxylated linear and ethoxylated branched long-chain alcohols, in particular mixtures of the aforementioned types.

In a further embodiment, b) is selected from ethoxylated iso-$C_{13}$-oxo alcohols and mixtures thereof.

In one or more embodiments, at least one alcohol b) is a branched, nonionic compound of the structural formula $RO(CH_2CH_2O)_xH$, where R is a $C_{13}$-alkyl radical, preferably an iso-$C_{13}$-alkyl radical, and where x=3, 5, 6, 6.5, 7, 8, 10, 12, 15 or 20, preferably x=10 used. Commercially, such an ethoxylated, alkyl-branched alcohol is available for example as Lutensol®TO10 (BASF SE).

In a further embodiment, b) is selected from mixtures comprising ethoxylated $C_{16}$-$C_{18}$-fatty alcohols and ethoxylated iso-$C_{13}$-oxo alcohols.

In a further embodiment, b) is selected from the above-described alcohols of the general formulae (4) or (5) of EP 761780 A2, p. 4 in their ethoxylated form.

c) Dendritic Polyetherpolyol

The polymers comprise, in polymerized-in form, at least one dendritic polyetherpolyol c).

As used herein, the term "dendritic" polyetherpolyols comprises quite generally polyetherpolyols which are characterized by a branched structure and a high functionality. As used herein, the "dendritic polymers" include dendrimeric polyetherpolyols, hyperbranched polyetherpolyols and structures derived therefrom.

"Dendrimers" are molecularly uniform macromolecules with a highly symmetrical structure. They are derived structurally from star polymers, the individual chains in each case being branched again in a star-like manner. Dendrimers are formed starting from small molecules by means of a continually repeating reaction sequence, during which ever higher branches result, at the ends of which are located in each case functional groups which are in turn the starting point for further branches. Thus, with each reaction step, the number of monomer end groups increases, ultimately producing a spherical tree structure. A characteristic feature of the dendrimers is the number of reaction stages carried out for their build-up, usually referred to as "generations". On account of their uniform build-up, dendrimers usually have a very narrow molecular mass distribution.

Dendritic polyetherpolyols c) of specific embodiments are both molecularly and structurally nonuniform hyperbranched polyetherpolyols which have side chains of differing length and branching and also a molar mass distribution. For the definition of hyperbranched polymers, reference is also made to P. J. Flory, J. Am. Chem. Soc. 1952, 74, 2718 and H. Frey et al., Chem. Eur. J. 2000, 6, No. 14, 2499.

In particular, so-called $AB_x$ monomers are suitable for the synthesis of hyperbranched polymers. These have two different functional groups A and B which are able to react together to form a linkage. The functional group A is present here only once per molecule, the functional group B, two or more times. The reaction of said $AB_x$ monomers with one another essentially produces uncrosslinked polymers with a regular arrangement of branching points. The polymers have virtually exclusively B groups at the chain ends. Further details can be found for example in Journal of Molecular Science, Rev. Macromol. Chem. Phys., C37(3), 555-579 (1997).

As used herein, dendritic polyetherpolyols c) are polyetherpolyols which, besides the ether groups which form the polymer backbone, have, in the terminal or lateral position, on average at least 3, preferably at least 4, further preferably at least 5 and in particular at least 6, OH groups per molecule. The dendritic polyetherols c) have on average not more than 500, preferably not more than 250, further preferably not more than 100 and in particularly not more than 50, terminal- or lateral-position functional OH groups per molecule.

In one or more embodiments, the dendritic polyetherpolyol c) is a condensation product of, on average, at least 3, particularly preferably at least 4, in particular at least 5 and most preferably at least 6, di-, tri- or higher-functional alcohols.

In one or more embodiments, the dendritic polyetherpolyol c) is the condensation product of, on average, at least 3, particularly preferably at least 4, specifically at least 5 and in particular at least 6, tri- or higher-functional alcohols.

In one or more embodiments, dendritic polyetherpolyols c) are hyperbranched polyetherpolyols. Dendritic polyetherpolyols are preferably uncrosslinked polymer molecules with hydroxyl and ether groups which are either structurally and molecularly nonuniform (hyperbranched polyetherpolyols), or else are structurally and molecularly uniform (dendrimeric polyetherpolyols).

Hyperbranched polyetherpolyols can be constructed starting from a central molecule analogously to dendrimers, but with nonuniform chain length of the branches. They may, on the other hand, also have linear areas with functional side groups.

As used herein, "hyperbranched" is understood as meaning that the degree of branching (for the definition of the degree of branching see H. Frey et al., Acta Polym. 1997, 48, 30), i.e. the average number of dendritic linkages plus average number of end groups per molecule, divided by the sum of the average number of dendritic, linear and terminal linkages per molecule, multiplied by 100, is 10 to 99.9%, preferably 20 to 99%, particularly preferably 20 to 95%.

The hyperbranched polyetherpolyols c) of one or more embodiments have a degree of branching of from 10 to 99.9%, preferably from 20 to 99%, particularly preferably from 20 to 95%.

As used herein, "dendrimer" means that a polymer molecule has a degree of branching of more than 99.9 to 100%.

The preparation of dendritic polyetherpolyols starting from glycerol is known. U.S. Pat. No. 3,932,532 and DE 10307172 describe the preparation of hyperbranched polyetherpolyols from glycerol by alkali catalysis. DE 10307172 describes the polycondensation of glycerol in the presence of acidic catalysts, for example HCl, $H_2SO_4$, sulfonic acid or $H_3PO_4$.

WO 2004/074346 describes the alkaline polycondensation of glycerol and the subsequent reaction of the resulting condensation product under acidic conditions with a fatty alcohol. This gives a polyglycerol modified with fatty alcohol.

Reference is made to the aforementioned disclosures.

Of suitability according to one or more embodiments as dendritic polyetherpolyols c) are dendritic polyglycerols, i.e. hyperbranched polyglycerol and polyglycerol dendrimers.

Suitable hyperbranched polyglycerols are, for example, polyglycerol ethers based on glycidol, as described in DE 19947631 and DE 10211664. The preparation takes place by the ring-opening reaction of glycidol, optionally in the presence of a polyfunctional starter molecule. Reference is made to these disclosures.

Polyglycerol dendrimers are described, for example, by Haag et al., J. Am. Chem. Soc. 2000, 122, 2954-2955, to which reference is hereby made.

Of suitability according to on or more embodiments as dendritic polyetherpolyols c) are also the polyetherpolyols disclosed in WO 00/56802, to which reference is hereby made. The dendritic polyetherpolyols c) described therein are obtainable by ring-opening polymerization of 1-ethyl-1-hydroxymethyloxetane with specific catalysts. The resulting polymer backbone consists of trimethylolpropane units.

Of suitability according to one or more embodiments as dendritic polyetherpolyols c) are also those described by Nishikubo et al., Polymer Journal 2004, 36 (5) 413, to which reference is hereby made. The dendritic polyetherpolyols c) described therein are obtainable by ring-opening polymerization of 3,3-bis(hydroxymethyl)oxetane.

Of suitability according to on or more embodiments as dendritic polyetherpolyols c) are also the polyetherpolyols which are obtainable by the joint ring-opening polymerization of 1-ethyl-1-hydroxymethyloxetane and 3,3-bis(hydroxymethyl)oxetane, as described by Chen et. al, J. Poly. Sci. Part A: Polym. Chem. 2002, 40, 1991, to which reference is hereby made.

Suitable dendritic hyperbranched polyetherpolyols are also described, for example, in WO 2009/101141 A1.

A process for the preparation of dendritic polyetherols is described therein, in which at least one tri- or higher-functional alcohol and optionally further di- and/or monofunctional alcohols and/or modifying reagents are reacted with the help of acidic catalysts.

Tri- and higher-functional alcohols which can be used are, for example, triols, such as trimethylolmethane, trimethylolethane, trimethylolpropane (TMP), 1,2,4-butanetriol, trishydroxymethyl isocyanurate, trishydroxyethyl isocyanurate (THEIC). Tetrols can likewise be used, such as bis-trimethylolpropane (di-TMP) or pentaerythritol. Furthermore, higher-functional polyols, such as bis-pentaerythritol (di-penta) or inositols can also be used. Furthermore, it is also possible to use alkoxylation products of the aforementioned alcohols and also of glycerol, preferably having 1-40 alkylene oxide units per molecule. As tri- and higher-functional alcohols, particular preference is given to using aliphatic alcohols and in particular those with primary hydroxyl groups, such as trimethylolmethane, trimethylolethane, trimethylolpropane, di-TMP, pentaerythritol, di-penta and alkoxylates thereof with 1-30 ethylene oxide units per molecule, and glycerol ethoxylates with 1-30 ethylene oxide units per molecule. Very particular preference is given to using trimethylolpropane, pentaerythritol and ethoxylates thereof having, on average, 1-20 ethylene oxide units per molecule, and glycerol ethoxylate with 1-20 ethylene oxide units per molecule. The specified alcohols can likewise be used in a mixture.

The tri- and higher-functional alcohols can also be used in a mixture with difunctional alcohols. Examples of suitable compounds with two OH groups comprise ethylene glycol, diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, hexanediol, dodecanediol, cyclopentanediol, cyclohexanediol, cyclohexanedimethanol, bis(4-hydroxycyclohexyl)methane, bis(4-hydroxycyclohexyl)ethane, 2,2-bis(4-hydroxycyclohexyl)propane, difunctional polyetherpolyols based on ethylene oxide, propylene oxide, butylene oxide or mixtures thereof, or polytetrahydrofuran. The difunctional alcohols can of course also be used in mixtures.

The diols serve for the fine adjustment of the properties of the polyetherpolyol. If difunctional alcohols are used, the ratio of difunctional alcohols to the tri- and higher-functional alcohols is set by the person skilled in the art depending on the desired properties of the polyether. As a rule, the amount of the difunctional alcohol(s) is 0 to 99 mol %, preferably 0-80, particularly preferably 0-75 mol % and very particularly preferably 0-50 mol %, with regard to the total amount of all alcohols. In this connection, as a result of the alternate addition of tri- and higher-functional alcohols and diols in the course of the reaction, it is also possible to obtain block copolyethers, for example diol-terminated polyethers.

As regards the building blocks for dendritic polyetherpolyols c), reference may be made to the disclosure in WO 2009/101141 p. 4, line 27 to p. 5, line 42, to which reference is made in its entirety.

As regards the synthesis of these dendritic polyetherpolyols c) by acidic catalysis, reference may be made to the disclosure in WO 2009/101141 p. 6, line 1 to p. 7, line 8, to which reference is made here in its entirety.

As regards further reaction conditions of the synthesis of these dendritic polyetherpolyols c), reference may be made to the disclosure of WO 2009/101141 p. 7, line 10 to p. 8, line 11, to which reference is made here in its entirety.

In a specific embodiment, the dendritic polyetherpolyols c) are obtainable by condensation of at least one tri- or higher-functional alcohol and optionally further di- and/or monofunctional alcohols and/or modifying reagents with the help of acidic catalysts.

In a specific embodiment, at least one dendritic polyetherpolyol c) is the condensation product of, on average, at least 3 di-, tri- or higher-functional alcohols.

In one or more embodiments, dendritic polyetherpolyols c) are obtainable by the acid-catalyzed polycondensation of trimethylolpropane.

In one or more embodiments, dendritic polyetherpolyols c) are obtainable by the acid-catalyzed polycondensation of trimethylolpropane, where at least some of the OH groups of the trimethylolpropane are alkoxylated.

In one or more embodiments, dendritic polyetherpolyols c) are also obtainable by the acid-catalyzed polycondensation of pentaerythritol.

In one or more embodiments, dendritic polyetherpolyols c) are also obtainable by the acid-catalyzed polycondensation of pentaerythritol, where at least some of the OH groups of the pentaerythritol have been alkoxylated.

In one or more embodiments, dendritic polyetherpolyols c) are also obtainable by the acid-catalyzed polycondensation of trimethyolpropane and triethylene glycol.

In one or more embodiments, dendritic polyetherpolyols c) are also obtainable by the acid-catalyzed polycondensation of trimethyolpropane and pentaerythritol.

In one or more embodiments, dendritic polyetherpolyols c) are also obtainable by the acid-catalyzed polycondensation of triethylene glycol and pentaerythritol.

In one or more embodiments, dendritic polyetherpolyols c) have a number-average molecular weight Mn of at least 300 g/mol, preferably at least 400 g/mol, further preferably at least 500 g/mol.

Modified Dendritic Polyetherpolyols c)

Suitable dendritic polyetherpolyols c) are also those dendritic polyetherpolyols c) which, in addition to the hydroxyl groups, comprise further functional groups which are preferably obtained by modifying at least some of the hydroxyl groups.

Such further functional groups comprise mercapto groups, primary, secondary or tertiary amino groups, ester groups, carboxylic acid groups or derivatives thereof, sulfonic acid groups or derivatives thereof, phosphonic acid groups or derivatives thereof, silane groups, siloxane groups, aryl radicals or short- or long-chain alkyl radicals.

Modifying reagents are used for the modification. These are compounds which have at least one such further functional group and at least one group reactive toward alcohol. Groups reactive toward alcohol are, for example, isocyanate groups, acid groups, acid derivatives or epoxide groups.

Compound c) can be modified prior to the polymerization by reacting at least some of its OH groups. This is possible either by preparing c) in the presence of modifying reagents or by modifying compound c) following its preparation. Both options are described in WO 2009/101141, p. 8, 1.13 to p. 9, 1.42, to which reference is hereby made.

The modifying reagents can be added before or during the preparation of the polyetherpolyols c) starting from for example tri- or higher-functional alcohols.

If the tri- or higher-functional alcohol or the alcohol mixture is reacted in the presence of modifying reagents in one step, then a polyetherpolyol is obtained with randomly distributed functionalities different from hydroxy groups.

Such a functionalization can be achieved for example by adding modifying reagents which carry mercapto groups, primary, secondary or tertiary amino groups, ester groups, carboxylic acid groups or derivatives thereof, sulfonic acid groups or derivatives thereof, phosphonic acid groups or derivatives thereof, silane groups, siloxane groups, aryl radicals or short- or long-chain alkyl radicals.

For the modification with mercapto groups, mercaptoethanol for example can be used as modifying reagent.

Tertiary amino groups can be produced for example by incorporating alcohols containing amino groups, such as triethanolamine, tripropanolamine, triisopropanolamine, N-methyldiethanolamine, N-methyldipropanolamine or N,N-dimethylethanolamine.

By adding dicarboxylic acids, tricarboxylic acids, dicarboxylic acid esters, such as for example adipic acid, dimethyl terephthale or tricarboxylic acid esters, it is possible to produce ester groups. Furthermore, ester groups can be obtained by reacting the OH groups with lactones, specifically with caprolactone. As a result of reaction with long-chain alkanols or alkanediols, it is possible to introduce long-chain alkyl radicals.

The reaction with alkyl or aryl isocyanates, diisocyanates or oligoisocyanates generates corresponding polyethers having urethane groups.

Subsequently functionalized dendritic polyetherpolyols c) are obtainable, for example, by reacting the dendritic polyetherpolyol in an additional process step with a modifying reagent reactive towards the OH groups of the dendritic polyetherpolyol.

The dendritic polyetherpolyols c) can be modified for example by adding modifying reagents comprising acid, acid halide or isocyanate groups.

Dendritic polyetherpolyols c) comprising acid groups are obtainable, for example, by reacting at least some of the OH groups with compounds comprising anhydride groups.

Dendritic polyetherpolyols c) comprising ester groups are obtainable, for example, by reacting at least some of the OH groups with caprolactone. The length of the ester chains can be controlled through the use amount of caprolactone.

Dendritic polyetherols c) with polyalkylene oxide chains are obtainable by reacting the dendritic polyetherols c) with alkylene oxides, for example ethylene oxide, propylene oxide, butylene oxide or mixtures thereof. Provided are polymers where the dendritic polyetherpolyol c) comprises polyalkylene oxide chains.

The novel polyurethane thickeners based on dendritic polyetherpolyols preferably have a large number of hydrophobic end groups, such as for example ethoxylated fatty radicals, and therefore have a considerably higher thickening power compared to the known polyurethane thickeners.

d) Polyol Different from b) and c)

The polymers according to on or more embodiments optionally comprise, in polymerized-in form, at least one compound d), different from b) and c), with a molecular weight of at least 200 g/mol, preferably at least 1500 g/mol.

Compound d) comprises, per molecule, at least two OH groups and at least two groups selected from ether groups and esters groups.

Compound d) is preferably selected from polyetherols, polyesterols and polyetheresterols.

In one or more embodiments, compound d) has a number-average molecular weight $M_n$ of from 1500 to 20 000 g/mol, preferably from 4000 to 12 000 g/mol.

Suitable compounds d) are, for example, the polymerization products of ethylene oxide, the mixed or graft polymerization products thereof, and the polyethers obtained by condensation of polyhydric alcohols or mixtures thereof and the polyethers obtained by ethoxylation of polyhydric alcohols, amides, polyamides and aminoalcohols. Examples thereof are, for example, polyethylene glycols, addition products of ethylene oxide onto trimethylolpropane, EO-PO block copolymers, OH-terminated polyesters such as, for example, those of the polyfunctional polycaprolactone type.

In one or more embodiments, compounds d) are polyetherpolyols. These are polyols which comprise, per molecule, at least two OH groups and at least two functions —O-(ether groups). These polyetherpolyols are generally so hydrophilic that they are water-soluble at room temperature (20° C.).

In a specific embodiment, compounds d) comprise, per molecule, on average from 30 to 450 $CH_2CH_2$—O— units (EO units). Preferred compounds d) are thus polyols of the general formula HO—$(CH_2$—$CH_2$—$O)_n$—H, where n can assume the values 30 to 450. These are usually condensation products of ethylene oxide with ethylene glycol or water.

In one or more embodiments, polyethylene glycols d) have a molecular weight $M_n$ in the range from 1500 to 20 000 g/mol, particularly preferably from 1500 to 12 000 g/mol, in particular from 4000 to 12 000 g/mol.

Suitable compounds d) are also ethylene oxide-propylene oxide block copolymers, such as, for example, EO-PO block copolymers of the general formula HO-$(EO)_m$—$(PO)_n$—$(EO)_o$—H, where m and o, independently of one another, are integers in the range from 10 to 100, preferably from 20 to 80, n is an integer in the range from 5 to 50, preferably from 20 to 40, and where m, n and o are selected such that HO-$(EO)_m$—$(PO)_n$-$(EO)_o$—H is water-soluble.

In one or more embodiments, the polyetherols d) have a molecular weight $M_n$ in the range from 1500 g/mol to 15,000 g/mol.

In a further embodiment, the polyetherols d) have a molecular weight $M_n$ in the range from 4000 g/mol to 12,000 g/mol.

In a further embodiment, the polyetherols d) have a molecular weight $M_n$ in the range from 200 g/mol to 1500 g/mol.

In a specific embodiment, the polyetherols d) have a molecular weight $M_n$ in the range from 6000 g/mol to 12,000 g/mol.

In a specific embodiment, the polyetherols d) have a molecular weight $M_n$ in the range from 6000 g/mol to 10,000 g/mol.

In one or more embodiments, the polyetherols d) have a molecular weight $M_n$ of about 10,000 g/mol.

In a specific embodiment, the polyetherols d) have a molecular weight $M_n$ of about 6000 g/mol.

In a further specific embodiment, the polyetherols d) have a molecular weight $M_n$ of about 9000 g/mol.

In one or more embodiments, no compounds d) are used for preparing the polymers. In this way, polymers with a low melt viscosity are obtained which can be handled easily in pure form. The viscosity increase arises only after adding water. Thus, firstly an easy-to-handle thickener preproduct is obtained, which only has a thickening effect upon the addition of water, i.e. for example when used in cosmetic preparation.

e) Further Compounds with Groups Reactive Toward Isocyanate

The polymers according to one or more embodiments optionally comprise further compounds e), different from a) to d), with in the region of 1 to 9 groups reactive toward isocyanate groups per molecule, polymerized-in.

Compounds with groups reactive toward isocyanate groups are preferably selected from compounds with hydroxyl groups such as, for example, alcohols, compounds with amino groups, such as, for example, amines and compounds with hydroxyl groups and amino groups, such as, for example, aminoalcohols.

Examples of compounds e) with up to 8 hydroxyl groups per molecule are disclosed, for example, in EP 1584331A1, paragraph [0039], to which reference is hereby made.

Suitable compounds e) with amino groups are, for example, ethylenediamine, diethylene triamine and propylenediamine.

Suitable compounds e) with hydroxyl groups and amino groups are, for example, ethanolamine and diethanolamine.

In a specific embodiment, polymers comprise, in polymerized-in form,
a) at least one polyisocyanate, preferably at least one diisocyanate,
b) at least one alcohol of the general formula I

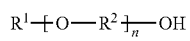  (I)

where
$R^1$ is selected from $C_6$-$C_{40}$-alkyl, preferably $C_{12}$-$C_{30}$-alkyl,
$R^2$ is selected from —$CH_2$—$CH_2$—, $CH(CH_3)$—$CH_2$— and mixtures thereof, preferably —$CH_2$—$CH_2$—,
n 3 to 100, preferably 10 to 20,
c) at least one dendritic polyetherpolyol,
d) at least one compound, different from b) and c), with a molecular weight $M_n$ in the range from 1500 g/mol to 20 000 g/mol, comprising
  i) at least two OH groups and
  ii) at least two ether groups, preferably at least one polyethylene glycol with $M_n$ in the range from 1500 g/mol to 12,000 g/mol.

In a specific embodiment, polymers comprise, in polymerized-in form,
a) at least one diisocyanate,
b) at least one alcohol of the general formula I

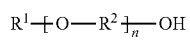  (I)

where
$R^1$ is selected from linear and/or branched $C_{12}$-$C_{30}$-alkyl,
$R^2$ is —$CH_2$—$CH_2$—,
n 3 to 100,
c) at least one dendritic polyetherpolyol where $M_n$ is at least 300 g/mol and comprising at least 5 OH groups per molecule,
d) at least one polyethylene glycol with $M_n$ in the range from 1500 g/mol to 12,000 g/mol.

The polymers according to one or more embodiments can comprise the components a), b) and c) in the following ratios (mol to mol):

if the polymers comprise compound d) polymerized-in:
a:b from 10:1 to 1:1.9; preferably 5:1 to 1:1
b:c from 25:1 to 1:1; preferably 10:1 to 1.5:1
a:d from 10:1 to 1:1.9; preferably 5:1 to 1:1

If the polymers of other embodiments comprise no d) polymerized-in:, then components a), b) and c) can be present in the following ratios (mol to mol):
a:b from 1.5:1 to 1:1.9; preferably 1.2:1 to 1:1.5
b:c from 25:1 to 1:1; preferably 10:1 to 1.5:1

Compound e) is preferably polymerized-in in such an amount that from 0 to 50 mol %, particularly preferably from 0 to 25 mol %, very particularly preferably from 0 to 10 mol %, of all of the groups in components b) to e) that are reactive toward isocyanate groups come from e).

In one or more embodiments, e) is polymerized-in in an amount such that from 0 to 1 mol % of all groups of components b) to e) that are reactive toward isocyanate groups come from e).

In a further embodiment, no compound e) is polymerized-in.

Processes for the Preparation

Further provided are processes for the preparation of the polymers provided herein. These processes are described below. The individual reaction steps are provided with Roman numerals. Steps with higher numerals are carried out, in terms of time, after steps with lower numerals.

To prepare the polymers, the components a) to e) can be polymerized in the presence of a solvent different from a) to e). Solvents are understood here as meaning a compound that is inert toward a) to e) in which the starting compounds a) to e), the resulting intermediates and the polymers according to embodiments are soluble. Soluble means that at least one 1 g, preferably at least 10 g, of the compound in question dissolves in 1 liter of solvent under standard conditions to give a solution that is clear to the human eye.

Suitable solvents are, for example, xylene, toluene, acetone, tetrahydrofuran (THF), butyl acetate, N-methylpyrrolidone and N-ethylpyrrolidone.

In one or more embodiments, the polymers are prepared from the compounds a) to e) essentially in the absence of solvents. Essentially in the absence of solvents means that, with regard to the total amount of the compounds a) to e), the polymerization is carried out in the presence of less than 10%, preferably less than 5% by weight, of a solvent different from a) to e).

For preparing the polymers, all catalysts customarily used in polyurethane chemistry are in principle suitable.

Such suitable catalysts and also the amount thereof, solvents and type of addition are described for example in WO 2009/135856, p. 11, 1.35 to p. 12, 1.42, to which reference is hereby made.

In one or more embodiments, the catalysts are zinc carboxylates, in particular selected from zinc 2-ethylhexanoate, zinc n-octanoate, zinc n-decanoate, zinc neodecanoate, zinc ricinoleate and zinc stearate. Zinc neodecanoate is particularly preferably used.

Suitable catalysts are also alkali(ne earth) metal salts of inorganic acid or of carboxylic acids such as, for example, potassium salts of acetic acid, citric acid, lactic acid, oxalic acid.

In one or more embodiments, all of the compounds used in the process are essentially anhydrous. "Essentially anhydrous" means that the water content of all of the compounds used in the process is less than 5% by weight, preferably less than 1% by weight, particularly preferably less than 0.1% by weight, based on the total amount of the respective compound.

Methods of removing water from the compounds before they are brought into contact with the compounds comprising NCO groups are customary and known to the person skilled in the art.

In one or more embodiments, to prepare the polymers,
I) d) is introduced as initial charge,
II) the addition of a) is started,
II) upon reaching an NCO value in the range from 99.9 to 0.1% of the starting value, preferably from 80 to 5% of the starting value, the addition of b) and c) is started approximately simultaneously.

In a specific embodiment, to prepare the polymers;
I) d) is introduced as initial charge,
II) the addition of a) is started,
III) upon reaching an NCO value in the range from 99.9 to 0.1% of the starting value, preferably from 80 to 5% of the starting value, the addition of b) is started,
IV) upon reaching an NCO value in the range from 95 to 5% of the starting value, preferably 50 to 5% of the starting value, the addition of c) is started.
Step IV) takes placed after step III).

In a further embodiment, to prepare the polymers,
I) the component b) is introduced as initial charge,
II) the addition of component a) is started,
III) upon reaching an NCO value in the range from 99.9 to 0.1% of the starting value, preferably from 80 to 5% of the starting value, very particularly preferably from 50 to 5% of the starting value, the addition of component c) is started.

Also provided is a process for the preparation of the polymers, comprising the steps
I) introduction of b) as initial charge,
II) addition of a),
III) start of the addition of c) if the NCO value is in the range from 99.9 to 0.1, preferably from 80 to 5, further preferably from 50 to 5%, of the starting value.

In one or more embodiments, the polymer obtainable by this process has, based on its total weight, less than 5% by weight, preferably less than 1% by weight and in particular 0% by weight, of compound d) polymerized-in.

The NCO value (isocyanate content) was determined titrimetically in accordance with DIN 53185.

Polymer-analogous Modification of the Polymers

In a specific embodiment, the dendritic polyetherpolyol c) comprises free OH groups after the polymerization. These bring about increased solubility of the polymers in polar solvents, in particular in alcohols and water, compared with conventional associative thickeners. The free OH groups of the polymerized-in compound c) also have a positive influence on the structure and the visual appearance of the preparations comprising the polymers according various embodiments.

In one or more embodiments, in the region of 5 to 95 mol %, preferably 25 to 75 mol %, of the OH groups originally present in c) are also still present, i.e. unreacted, in the polymers according various embodiments after the polymerization.

Thus, also provided are polymers in which in the region of 5 to 95% of the OH groups present in c) before the polymerization are also present as OH groups after the polymerization.

A thickening effect sufficient for certain applications can be achieved above a conversion of just 5 mol % of the OH groups originally present in c), i.e. with 95 mol % OH groups still present.

Also provided are polymers in which in the region of 75 to 95% of the OH groups present in c) before the polymerization are also present as OH groups after the polymerization.

In another embodiment, in the region of 0 to 50 mol % of the OH groups originally present in c) are also still present in the polymers according to one or more embodiments.

Furthermore also provided are polymers which are obtainable by the reaction of at least some of the free OH groups of the polymerized-in compound c) of the polymer with compounds reactive toward OH groups.

The polymerized-in compound c) can be modified by reacting the polymer according to various embodiments in an additional process step with suitable modifying reagents which are able to react with the OH groups of c).

The remaining OH groups in the polymerized-in compound c) can be modified for example by adding modifying reagents comprising acid, acid halide or isocyanate groups. A functionalization of the polymerized-in compound c) with acid groups can take place for example by reacting their OH groups with compounds comprising anhydride groups. Ester groups can be introduced subsequently for example through reaction with caprolactone. Here, the length of the ester chains can be controlled through the amount of caprolactone used.

Furthermore, the polymerized-in compound c) can also be functionalized through reaction with alkylene oxides, for example ethylene oxide, propylene oxide, butylene oxide or mixtures thereof.

Also provided are polymers obtainable by functionalization of the polymerized-in compound c) with substances reactive toward OH groups which, besides at least one group reactive toward OH groups, comprise further groups such as carboxylate, sulfonate, diol or polyol.

Also provided are polymers obtainable by functionalization of the polymerized-in compound c) with substances reactive toward OH groups which, besides at least one group reactive toward OH groups, comprise sugar molecules.

Also provided are polymers obtainable by functionalization of the polymerized-in compound c) with substances reactive toward OH groups which, besides at least one group reactive toward OH groups, comprise polar polymer chains such as, for example, polyacrylic acid chains or polyalkylene glycol chains.

Also provided are polymers obtainable by functionalization of the polymerized-in compound c) with substances reactive toward OH groups which, besides at least one group reactive toward OH groups, comprise nonpolar polymer chains such as, for example, polyisobutene chains.

Also provided are polymers obtainable by functionalization of the polymerized-in compound c) with substances reactive toward OH groups which, besides at least one group reactive toward OH groups, comprise silicone chains.

Also provided are polymers obtainable by functionalization of the polymerized-in compound c) with substances reactive toward OH groups which, besides at least one group reactive toward OH groups, comprise amphiphilic surfactant chains.

The aforementioned polymers are also obtainable by carrying out the functionalization of the polymerized-in compound c) in two steps:
I) reaction of at least some of the free OH groups of the polymerized-in compound c) with a polyisocyanate, preferably with a diisocyanate, particularly preferably with an asymmetrical diisocyanate which has 2 different reactive NCO groups, such as, for example, isophorone diisocyanate or toluene 2,4-diisocyanate,
II) reaction of the remaining NCO groups with substances that are reactive toward NCO groups, such as, for example, substances comprising hydroxyl groups or preferably amino groups.

Functional groups such as carboxylate, sulfonate, diol, sugar, polar and nonpolar polymer chains, surfactant chains can thus be bonded to the polymerized-in, NCO-functionalized compound c) via a hydroxyl group or an amino group.

Also provided is the use of the polymers according to various embodiments for preparing aqueous preparations. Preference is given here to preparations which comprise at least 5% by weight, in particular at least 20% by weight, very particularly preferably at least 30% by weight and most preferably at least 70% by weight, of water. Preference is given to preparations which comprise at most 95% by weight, particularly preferably at most 90% by weight and in particular at most 85% by weight, of water.

The preparations comprising water may be, for example, solutions, emulsions, suspensions or dispersions.

In addition to the polymers provided herein, further substances can be used for preparing the preparations, such as e.g. customary auxiliaries (for example dispersants and/or stabilizers), surfactants. preservatives, antifoams, fragrances, wetting agents, UV filters, pigments, emollients, active ingredients, further thickeners, dyes, softeners, humectants and/or other polymers.

Cosmetic Preparations

Further provided are cosmetic preparations comprising at least one polymer according to embodiments provided herein.

For the use in cosmetic preparations, preference is given to those polymers which are prepared without using a catalyst comprising tin.

One advantage of the polymers provided herein when used in cosmetic preparations is that their thickening ability is in each case virtually unchanged even
1) after the addition of salts or pigments in an amount of at least 1, preferably at least 2% by weight, based on the preparation,
2) up to temperatures of about 50° C. and
3) in the case of changes in the pH in the range from 2 to 13.

Cosmetic preparations which comprise the polymers provided herein have a more finely divided structure compared to preparations which comprise known thickeners as a result of the reduction in particle sizes.

The free OH groups attributable to the polymerized-in dendritic polyetherpolyol bring about a higher solubility in water.

The use of polymer-analogously polar modified polymers provided herein leads preferentially to emulsions of greater stability.

Also provided is the use of polymer-analogously polar modified polymers of one or more embodiments for increasing the compatibility with polar solvents such as, for example, low molecular weight monohydric alcohols such as e.g. ethanol or low molecular weight polyhydric alcohols such as, for example, propylene glycol or glycerol.

Likewise, provided is the use of polymer-analogously polar modified polymers of one or more embodiments for increasing the solubility of ingredients with limited solubility in water such as, for example, hydrophilic UV filters.

Further provided is the use of polymer-analogously polar modified polymers according one or more embodiments for increasing the water-binding capacity in the preparation and also following application to the skin (use of the polymers provided herein as moisturizers).

Further provided is the use of the polymer-analogously nonpolar modified polymers according to one or more embodiments for increasing the compatibility with nonpolar liquid phases such as, for example, cosmetic oils and silicone oils.

Likewise, provided is the use of polymer-analogously nonpolar modified polymers according to one or more embodiments for increasing the solubility of ingredients with limited solubility in oil such as, for example, hydrophobic UV filters.

Further provided is the use of polymer-analogously modified polymers of one or more embodiments for improving the dispersibility of particles in the preparation.

Further provided is a method for improving the skin feel, characterized in that the skin is brought into contact with a preparation comprising a polymer-analogously nonpolar modified polymer according to one or more embodiments.

By using subsequently amphiphilically modified polymers according to one or more embodiments it is possible to adjust the rheological behavior depending on the case.

The polymers provided herein can generally be used instead of the associative thickeners known from the prior art for cosmetic preparations.

Cosmetic preparations comprising an associative thickener based on polyurethane are described in detail in WO 2009/135857, p. 22 to 73. Preparations provided are the preparations described in WO 2009/135857, p. 87 to 114, with the proviso that the preparations according to the invention comprise a polymer provided herein instead of the polyurethane thickener referred to therein.

All preparations described in the publication IPCOM000181520D are also in accordance with the invention, with the proviso that the "polymer 1" specified therein is replaced by a polymer provided herein.

All of the preparations described in the publication IPCOM000181842D are also in accordance with the invention, with the proviso that the "polymer 1" specified therein is replaced by a polymer provided herein.

All of the preparations described in the publication IPCOM000183957D are also in accordance with the invention, with the proviso that the "polymer 1" specified therein is replaced by a polymer provided herein.

Without intending to limit the invention in any manner, embodiments will be more fully described by the following examples.

EXAMPLES

The molecular weights of the polymers A.1 to A.7 according to embodiments and also of the polymers according to Comparative Examples A.8 and A.9 was determined by GPC in tetrahydrofuran as solvent, standard: PMMA.

The molecular weight of the polyetherpolyol PE.1 was determined by GPC in hexafluoroisopropanol+0.05% trifluoroacetic acid potassium salt as solvent, standard: PMMA.

The OH number was determined in accordance with DIN 53240, Part 2.

All of the reactions were carried out under a protective-gas atmosphere (dried nitrogen).

The degree of functionalization in % indicates how much mol % of the OH groups originally present in compound c) were reacted during the polymerization.

Other data in % are all % by weight unless expressly stated otherwise.

Preparation of a Hyperbranched Polyetherpolyol from Pentaerythritol and Triethylene Glycol (PE.1)

The polymerization was carried out in a 4 liter four-neck glass flask equipped with a stirrer, reflux condenser and a distillation bridge with vacuum connection. The mixture of 1250.4 g of pentaerythritol (9.00 mol), 1393.3 g of triethylene glycol (9.00 mol) and 6.8 g of trifluoromethanesulfonic acid was evacuated and slowly heated to 200° C. by means of an oil bath at a pressure of 200 mbar. After reaching the reaction temperature, the reaction mixture was stirred for 4 h. The reaction mixture was then left to cool in vacuo. For the neutralization, 8.0 g of ethanolic KOH (5 molar) were added to the reaction solution and the mixture was stirred for 2 h.

The product was then stripped at 130° C. and at a subatmospheric pressure of up to 100 mbar for 4 h. The polyetherpolyol PE.1 ($M_n$=510 g/mol; $M_w$=3670 g/mol; OH number 675 mg KOH/g of polymer) was finally obtained as a high viscosity, pale brown colored liquid.

Synthesis Example 1

Preparation of a Polymer According an Embodiment Comprising a Hyperbranched Polyetherpolyol, Degree of Functionalization of the OH Groups 25%
(A.1)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 100 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB®Kat 616, TIB Chemicals, Mannheim), dissolved in 5 ml of xylene, and 6.72 g of hexamethylene diisocyanate, dissolved in 10 ml of xylene, the polymerization was started and the batch was run at an internal temperature of 50° C. to an isocyanate content of 0.40%. Then, 16.58 g of Lutensol®AT11 (BASF SE), dissolved in 20 ml of xylene, were added and the reaction mixture was further heated at 50° C. until the isocyanate content was 0.17%. 5.85 g of the hyperbranched polyetherpolyol PE.1, dissolved in 20 ml of THF, were then added and the reaction mixture was further heated at 50° C. until the isocyanate content was finally 0%. The solvents xylene and THF were subsequently largely removed by vacuum distillation at elevated temperature (ca. 60° C.) (residual content <100 ppm) and the residue was dissolved in 602.4 g of water. Then, 7.52 g of the preservative Euxyl®K701 and 80 mg of the stabilizer 4-hydroxy-TEMPO were added to the aqueous solution. After cooling to room temperature (25° C.), the polymer A.1 ($M_n$=14 500 g/mol; $M_w$=33 200 g/mol) was obtained in the form of an aqueous dispersion which had a solids content of 20.4%. The viscosity of a 10% strength aqueous solution of the branched polyetherpolyurethane A.1 was 15 000 mPa*s (shear rate 100 l/s) or 7000 mPa*s (shear rate 350 l/s).

Synthesis Example 2

Preparation of a Polymer According to an Embodiment Comprising a Hyperbranched Polyetherpolyol, Degree of Functionalization of the OH Groups 50% (A.2)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 110 ppm. The polymer solution was then cooled to 50° C. (internal temperature) and admixed with 107 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB Kat 616, TIB Chemicals, Mannheim), dissolved in 5 ml of xylene, and 6.72 g of hexamethylene diisocyanate, dissolved in 10 ml of xylene, the polymerization was started and the batch was run at an internal temperature of 50° C. to an isocyanate content of 0.40%. 16.58 g of Lutensol®AT11 (BASF SE), dissolved in 20 ml of xylene, were then added and the reaction mixture was further heated at 50° C. until the isocyanate content was 0.17%. 2.93 g of the hyperbranched polyetherpolyol PE.1, dissolved in 20 ml of THF, were then added and the reaction mixture was further heated at 50° C. until the isocyanate content was finally 0%. The solvents xylene and THF were subsequently largely removed by vacuum distillation at elevated temperature (ca. 60° C.) (residual content <100 ppm) and the residue was dissolved in 587.8 g of water. 7.35 g of the preservative Euxyl®K701 and 70 mg of the stabilizer 4-hydroxy-TEMPO were then added to the aqueous solution. After cooling to room temperature (25° C.), the polymer A.2 ($M_n$=15 000 g/mol; $M_w$=39 500 g/mol) was obtained in the form of an aqueous dispersion which had a solids content of 20.3%. The viscosity of a 10% strength aqueous solution of the branched polyetherpolyurethane A.2 was 25 000 mPa*s (shear rate 100 l/s) and 12 000 mPa*s (shear rate 350 l/s).

Synthesis Example 3

Preparation of a Polymer According to an Embodiment Comprising a Hyperbranched Polyetherpolyol, Degree of Functionalization of the OH Groups 100% (A.3)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 100 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB®Kat 616, TIB Chemicals, Mannheim), dissolved in 5 ml of xylene, and 6.72 g of hexamethylene diisocyanate, dissolved in 10 ml of xylene, the polymerization was started and the batch was run at an internal temperature of 50° C. to an isocyanate content of 0.40%. 16.58 g of Lutensol®AT11 (BASF SE), dissolved in 20 ml of xylene, were then added and the reaction mixture was further heated at 50° C. until the isocyanate content was 0.16%. 1.46 g of the hyperbranched polyetherpolyol PE.1, dissolved in 20 ml of THF, were then added and the reaction mixture was further heated at 50° C. until the isocyanate content was finally 0%. The solvents xylene and THF were subsequently largely removed by vacuum distillation at elevated temperature (ca. 60° C.) (residual content <100 ppm) and the residue was dissolved in 580.5 g of water. 7.26 g of the preservative Euxyl®K701 and 70 mg of the stabilizer 4-hydroxy-TEMPO were then added to the aqueous solution. After cooling to room temperature (25° C.), the polymer A.3 ($M_n$=17 100 g/mol; $M_w$=42 300 g/mol) was obtained in the form of an aqueous dispersion which had a solids content of 21.2%. The viscosity of a 5% strength aqueous solution of the branched polyetherpolyurethane A.1 was 9200 mPa*s (shear rate 100 l/s) and 4600 mPa*s (shear rate 350 l/s).

Synthesis Example 4

Preparation of a Polymer According to an Embodiment Comprising a Hyperbranched Polyetherpolyol, Degree of Functionalization of the OH Groups 50% (A.4)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca. 140° C. (internal temperature), 200 g of xylene were distilled off. The water content of the reaction mixture was then only still ca. 100 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB Kat 616, TIB Chemicals, Mannheim), dissolved in 5 ml of xylene, and 8.89 g of isophorone diisocyanate, dissolved in 10 ml of xylene, the polymerization was started and the batch was run at an internal temperature of 50° C. to an isocyanate content of 0.40%. 16.58 g of Lutensol®AT11 (BASF SE), dissolved in 20 ml of xylene, were then added and the reaction mixture was further heated at 50° C. until the isocyanate content was 0.17%. 2.93 g of the hyperbranched polyetherpolyol PE.1, dissolved in 20 ml of THF, were then added and the reaction mixture was further heated at 50° C. until the isocyanate content was finally 0%. The solvents xylene and THF were subsequently largely removed by vacuum distillation at elevated temperature (ca. 60° C.) (residual content <100 ppm) and the residue was dissolved in 596.5 g of water. 7.45 g of the preservative Euxyl®K701 and 80 mg of the stabilizer 4-hydroxy-TEMPO were then added to the aqueous solution. After cooling to room temperature (25° C.), the polymer A.4 ($M_n$=15 100 g/mol; $M_w$=41 300 g/mol) was obtained in the form of an aqueous dispersion which had a solids content of 19.8%. The viscosity of a 5% strength aqueous solution of the branched polyetherpolyurethane A.4 was 8200 mPa*s (shear rate 100 1/s) and 3500 mPa*s (shear rate 350 1/s).

Synthesis Example 5

Preparation of a Polymer According to an Embodiment Comprising a Hyperbranched Polyetherpolyol, Degree of Functionalization of the OH Groups 50% (A.5)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 100 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB Kat 616, TIB Chemicals, Mannheim), dissolved in 5 ml of xylene, and 8.89 g of isophorone diisocyanate, dissolved in 10 ml of xylene, the polymerization was started and the batch was run at an internal temperature of 50° C. to an isocyanate content of 0.40%. A mixture of 8.29 g of Lutensol®AT11 (BASF SE) and 7.17 g of Lutensol®TO10 (BASF SE), dissolved in 20 ml of xylene, was then added and the reaction mixture was further heated at 50° C. until the isocyanate content was 0.17%. 2.93 g of the hyperbranched polyetherpolyol PE.1, dissolved in 20 ml of THF, were then added and the reaction mixture was further heated at 50° C. until the isocyanate content was finally 0%. The solvents xylene and THF were then largely removed by vacuum distillation at elevated temperature (ca. 60° C.) (residual content <100 ppm) and the residue was dissolved in 589.1 g of water. 7.37 g of the preservative Euxyl®K701 and 70 mg of the stabilizer 4-hydroxy-TEMPO were then added to the aqueous solution. After cooling to room temperature (25° C.), the polymer A.5 ($M_n$=14 900 g/mol; $M_w$=38 200 g/mol) was obtained in the form of an aqueous dispersion which had a solids content of 20.4%. The viscosity of a 10% strength aqueous solution of the branched polyetherpolyurethane A.5 was 6700 mPa*s (shear rate 100 1/s) and 4600 mPa*s (shear rate 350 1/s).

Synthesis Example 6

Preparation of a Polymer According to an Embodiment Comprising a Hyperbranched Polyetherpolyol, Degree of Functionalization of the OH Groups 50% (A.6)

374.00 g of Lutensol®AT25 (BASF SE) were dissolved in 374.00 g of acetone under nitrogen in a 2 liter polymerization reactor (flat flange glass vessel with anchor stirrer). The polymer solution was then heated at 50° C. (internal temperature) and admixed with 259 mg of acetic acid in order to neutralize the amount of potassium acetate in the Lutensol®, which had been quantatively determined beforehand. By adding 4 mg of zinc neodecanoate (TIB Kat 616, TIB Chemicals, Mannheim) and 55.58 g of isophorone diisocyanate, dissolved in 55.58 g of acetone, the reaction was started and the batch was run at an internal temperature of 50° C. to an isocyanate content of 1.13%. 20.78 g of the hyperbranched polyetherpolyol PE.1, dissolved in 20.78 g of acetone, and a further 1.35 g of zinc neodecanoate (TIB Kat 616, TIB Chemicals, Mannheim), dissolved in 10.00 g of acetone, were then added and the reaction mixture was further heated at 50° C. until the isocyanate content was finally 0%. The solvent acetone was then largely removed by vacuum distillation at elevated temperature (ca. 60° C.) (residual content <100 ppm) and the residue was dissolved in 1000.0 g of water. 22.52 g of the preservative Euxyl®K701 and 230 mg of the stabilizer 4-hydroxy-TEMPO were then added to the aqueous solution. After cooling to room temperature (25° C.), the polymer A.6 ($M_n$=3700 g/mol; $M_w$=6500 g/mol) was obtained in the form of an aqueous dispersion which had a solids content of 31.2%. The viscosity of a 10% strength aqueous solution of the branched polyetherpolyurethane A.6 was 1160 mPa*s (shear rate 100 1/s) and 930 mPa*s (shear rate 350 1/s).

Synthesis Example 7

Preparation of a Polymer According to an Embodiment Comprising a Hyperbranched Polyetherpolyol, Degree of Functionalization of the OH Groups 50%; Subsequently Functionalized with Diethanolamine (A.7)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 100 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB®Kat 616, TIB Chemicals, Mannheim), dissolved in 5 ml of xylene, and 6.72 g of hexamethylene diisocyanate, dissolved in 10 ml of xylene, the polymerization was started and the batch was run at an internal temperature of 50° C. to an isocyanate content of 0.41%. 16.58 g Lutensol®AT11 (BASF SE), dissolved in 20 ml of xylene, were then added and the reaction mixture was further heated at 50° C. until the isocyanate content was 0.17%. 2.93 g of the hyperbranched polyetherpolyol PE.1, dissolved in 20 ml of THF, were then added and the reaction mixture was further heated at 50° C. until the isocyanate content was finally 0%. A further 3.91 g of isophorone diisocyanate, dissolved in 10 ml of xylene, were then added to the polymer solution obtained in this way and the batch was run to an isocyanate content of 0.15% in order to convert the OH groups of the already formed thickener molecule into isocyanate groups. 1.85 g of diethanolamine, dissolved in 10 ml of THF, were then added and the reaction was stopped. The solvents xylene and THF were then largely removed by vacuum distillation at elevated temperature (ca. 60° C.) (residual content <100 ppm) and the residue was dissolved in 610.9 g of water. 7.58 g of the preservative Euxyl®K701 and 80 mg of the stabilizer 4-hydroxy-TEMPO were then added to the aqueous solution. After cooling to room temperature (25° C.), the polymer A.7 post-functionalized with diol groups ($M_n$=13 800 g/mol; $M_w$=37 500 g/mol) was obtained in the form of an aqueous dispersion which had a solids content of 20.2%. The viscosity of a 10% strength aqueous solution of the post-functionalized, branched polyetherpolyurethane A.7 was 36 000 mPa*s (shear rate 100 l/s) (viscosity at shear rate 350 l/s could not be measured).

Comparative Example

Preparation of a PUR Associative Thickener Comprising Trimethylolpropane (Known Structure), Degree of Functionality of the OH Groups 100% (A.8)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 120 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB®Kat 616, TIB Chemicals, Mannheim), dissolved in 5 ml of xylene, and 6.72 g of hexamethylene diisocyanate, dissolved in 10 ml of xylene, the polymerization was started and the batch was run at an internal temperature of 50° C. to an isocyanate content of 0.40%. 16.58 g of Lutensol®AT11 (BASF SE), dissolved in 20 ml of xylene, were then added and the reaction mixture was further heated at 50° C. until the isocyanate content was 0.18%. 0.79 g of 1,1,1-tris(hydroxymethyl)propane (TMP), dissolved in 20 ml of THF, were then added and the reaction mixture was further heated at 50° C. until the isocyanate content was finally 0%. The solvents xylene and THF were then largely removed by vacuum distillation at elevated temperature (ca. 60° C.) (residual content <100 ppm) and the residue was dissolved in 577.1 g of water. 7.22 g of the preservative Euxyl®K701 and 70 mg of the stabilizer 4-hydroxy-TEMPO were then added to the aqueous solution. After cooling to room temperature (25° C.), the polymer A.8 ($M_n$=16 500 g/mol; $M_w$=39 500 g/mol) was obtained in the form of an aqueous dispersion which had a solids content of 20.5%. The viscosity of a 5% strength aqueous solution of the branched polyetherpolyurethane A.8 was 12 500 mPa*s (shear rate 100 l/s) and 7500 mPa*s (shear rate 350 l/s).

Comparative Example

Preparation of a PUR associative Thickener Comprising Ethylene Glycol (Linear Structure), Degree of Functionalization of the OH Groups 100% (A.9)

120.00 g of polyethylene glycol Pluriol®E6000 (BASF SE, molecular weight 6000 g/mol) were dissolved in 467.00 g of xylene under nitrogen in a 2 liter polymerization reactor (flat flange glass vessel with anchor stirrer). After heating the solution to ca.140° C. (internal temperature), 200 g of xylene were distilled off. The water content of the reaction mixture was then only still ca. 100 ppm. The polymer solution was then cooled to 50° C. (internal temperature) and admixed with 89 mg of acetic acid, dissolved in 5 ml of xylene, in order to neutralize the amount of potassium acetate in the polyethylene glycol, which had been quantitatively determined beforehand. By adding 360 mg of zinc neodecanoate (TIB®Kat 616, TIB Chemicals, Mannheim), dissolved in 5 ml of xylene, and 6.72 g of hexamethylene diisocyanate, dissolved in 10 ml of xylene, the polymerization was started and the batch was run at an internal temperature of 50° C. to an isocyanate content of 0.40%. 16.58 g of Lutensol®AT11 (BASF SE), dissolved in 20 ml of xylene, were then added and the reaction mixture was further heated at 50° C. until the isocyanate content was 0.18%. 0.55 g of monoethylene glycol, dissolved in 20 ml of THF, were then added and the reaction mixture was further heated at 50° C. until the isocyanate content was finally 0%. The solvents xylene and THF were then largely removed by vacuum distillation at elevated temperature (ca. 60° C.) (residual content <100 ppm) and the residue was dissolved in 575.9 g of water. 7.20 g of the preservative Euxyl®K701 and 70 mg of the stabilizer 4-hydroxy-TEMPO were then added to the aqueous solution. After cooling to room temperature (25° C.), the polymer A.9 ($M_n$=14 300 g/mol; $M_w$=33 500 g/mol) was obtained in the form of an aqueous dispersion which had a solids content of 19.9%. The viscosity of a 10% strength aqueous solution of the branched polyetherpolyurethane A.9 was 27 000 mPa*s (shear rate 100 l/s) (viscosity at shear rate 350 l/s could not be measured).

Cosmetic Preparations Based on Cremophor®A6/Cremophor®A25 or Stearate Comprising the Polymers A.1 to A.9 According to the Examples (Preparations FA.1.1-FA.1.9 and FA.2.1-FA.2.9)

The cosmetic preparations were prepared by adding the water phase B to the oil phase A and subsequently admixing the resulting O/W emulsion with the preservative (phase C). This gave the formulations FA.1.1-FA.1.9 based on a Cremophor®A6/A25 base (Tab. 1) and also the formulations FA.2.1-FA.2.9 based on a stearate base (Tab. 4).

The quantitative data for the polymers Examples A.1-A.9 in the formulations FA.1.1-FA.1.9 (Tab.1) and FA.2.1-FA.2.9 (Tab.4) represent the amounts of polymer.

TABLE 1

Formula parameters for the cosmetic formulations FA.1.1-FA.1.9 based on a Cremophor ® A6/A25 base.

| Phase | Ingredients | FA.1.1-1.9 * |
|---|---|---|
| Phase A | Cremophor ®A 6 | 2.0 g |
| | Cremophor ®A 25 | 2.0 g |
| | Lanette ®O | 2.5 g |
| | Paraffin oil | 5.0 g |
| | Luvitor ®EHO | 5.0 g |
| Phase B | One of the polymers A.1-A.9 | 0.5 g |
| | 1,2-Propylene glycol | 5.0 g |
| | Water | 77.5 g |
| Phase C | Euxyl ®K300 | 0.5 g |

* FA.1.8, FA.1.9 are comparative (not in accordance with the invention)

TABLE 2

Viscosities of the thickeners A.1-A.9 in water, as a function of the shear rate.

| | Polymer concentration | Viscosity [mPa * s] | |
|---|---|---|---|
| Polymer | in water [% by wt] | shear rate 100 1/s | shear rate 350 1/s |
| A.1 | 10 | 15 000 | 7000 |
| A.2 | 10 | 25 000 | 12 000 |
| A.3 | 5 | 9200 | 4600 |
| A.4 | 5 | 8200 | 3500 |
| A.5 | 10 | 6700 | 4600 |
| A.6 | 10 | 1160 | 930 |
| A.7 | 10 | 36 000 | n.d. |
| A.8 * | 5 | 12 500 | 7500 |
| A.9 * | 10 | 27 000 | not determined |

* comparative (not according to the invention)

TABLE 3

Viscosities of the cosmetic formulations FA.1.1-FA.1.9

| Formulation | Viscosity [Pa * s] in the presence of 2.0% NaCl |
|---|---|
| FA.1.1 | 13.5 |
| FA.1.2 | 19.2 |
| FA.1.3 | 30.0 |
| FA.1.4 | 10.5 |
| FA.1.5 | 6.1 |
| FA.1.6 | n.d. |
| FA.1.7 | 19.5 |
| FA.1.8 * | 30.0 |
| FA.1.9 * | 20.0 |

* comparative (not according to the invention)

Structure in the case of Comparative Example FA.1.8 very poor (grainy) despite high viscosity.

The polymer of one embodiment with completely reacted OH groups A.3 achieves the highest viscosity (30.0 Pa*s), i.e. the same value as polymer A.8. However, the corresponding preparation FA.1.8 has a considerably poorer structure; the structure of the preparation FA.1.3 is significantly better on account of the polymerized-in hyperbranched polyether-polyol.

The corresponding linear comparative structure A.9 produces a viscosity (FA.1.9) of 20.0 Pa*s and is therefore comparable with the viscosity of the polymer A.2 (FA.1.2) with 19.2 Pa*s. The decisive advantage of the polymer A.2 according to one embodiment over A.9 consists, for a comparable viscosity, in the possibility of the functionalization and tailoring of the polymer architecture, since 50% of the originally present OH groups of the polymerized-in compound c) are still present as OH groups.

TABLE 4

Formula parameters for the cosmetic formulations FA.2.1-FA.2.9 based on a stearate base.

| Phase | Ingredients | FA.2.1-FA.2.9 * |
|---|---|---|
| Phase A | Cutina ®GMS | 2.0 g |
|  | Lanette ® 18 | 2.0 g |
|  | Dow Corning ® 345 Fluid | 3.0 g |
|  | Cetiol ®OE | 3.0 g |
|  | Abil ®350 | 2.0 g |
|  | Dry Flo | 1.0 g |
|  | Myrj 52 | 2.0 g |

TABLE 4-continued

Formula parameters for the cosmetic formulations FA.2.1-FA.2.9 based on a stearate base.

| Phase | Ingredients | FA.2.1-FA.2.9 * |
|---|---|---|
| Phase B | One of the polymers A.1-A.9 | 0.5 g |
|  | Glycerol | 5.0 g |
|  | Water | 79.0 g |
| Phase C | Euxyl ®K300 | 0.5 g |

* FA.2.8, FA.2.9 are comparative (not according to the invention)

TABLE 5

Viscosities of the cosmetic formulations FA.2.1-FA.2.9

| Formulation | Viscosity [Pa * s] in the presence of 2.0% NaCl |
|---|---|
| FA.2.1 | 6.8 |
| FA.2.2 | 9.0 |
| FA.2.3 | 8.7 |
| FA.2.4 | 5.7 |
| FA.2.5 | 10.0 |
| FA.2.6 | not determined |
| FA.2.7 | 7.1 |
| FA.2.8 * | 9.0 |
| FA.2.9 * | 4.4 |

* comparative (not according to the invention)

Structure in the case of Comparative Example FA.2.8 very poor (grainy) despite high viscosity.

Here, the structures A.2, A.3 (according to the invention) and A.8 (not according to the invention) permit similar viscosities of the cosmetic preparations of ca. 9 Pa*s. The polymer A.2 according to the invention can be subsequently modified, in contrast to A.8. The structure of the preparation obtainable with polymer A.3 is considerably better than that which is obtained with A.8.

Application Examples

Further typical preparations according to various embodiments are described below, without however restricting the invention to these examples.

Besides the preparation of the cosmetic preparations described here, the polymers A.1, A.2, A.3, A.4, A.5, A.6 or A.7, and combinations thereof can be added to the respective emulsion also after combining water and oil phase at 60-80° C. or to the cooled emulsion at about 40° C.

Also provided is the subsequent addition of the polyurethanes obtainable according to embodiments to a cosmetic preparation in order to establish the desired viscosity.

The percentage data are % by weight, unless expressly described otherwise.

| | O/W emulsion | | | | |
|---|---|---|---|---|---|
| Phase | Ingredient/INCI | F.3.1 | F.3.2 | F.3.3 | F.3.4 | F.3.5 |
| A | Aqua | ad 100 | ad 100 | ad 100 | ad 100 | ad 100 |
|  | Glycerin | 3.0 | 5.50 | 4.50 | 5.00 | 3.5 |
|  | Polymer A.1 | 3.0 | 1.5 | 0.8 | 2.0 | 2.5 |
|  | Hydroxyethyl Acrylate/ Sodium Acryloyldimethyl Taurate Copolymer, Squalane, Polysorbate 60 | | 1.0 | | 0.5 | |
| B | Glyceryl Stearate Citrate | 1.80 | 2.00 | 3.00 | 1.50 | 2 |
|  | Sucrose Stearate | 1.00 | 1.20 | 2.00 | 2.20 | 1.5 |
|  | Cetearyl Alcohol | 1.80 | 2.00 | 1.50 | 2.40 | 2.8 |
|  | Ethylhexyl Palmitate | 6.00 | 5.00 | 3.50 | 3.00 | 5.5 |
|  | Caprylic/Capric Triglyceride | 5.00 | 5.00 | 1.00 | 2.00 | 3.5 |
|  | Octyldodecanol | 1.50 | 3.00 | 2.40 | 5.0 | 4.6 |
|  | Dimethicone | 0.20 | 0.50 | 2.00 | 1.80 | 1.4 |

O/W emulsion (continued)

| Phase | Ingredient/INCI | F.3.1 | F.3.2 | F.3.3 | F.3.4 | F.3.5 |
|---|---|---|---|---|---|---|
| C | Ammonium Acryloyldimethyltaurate/ VP Copolymer | | | 0.5 | 0.1 | |
|  | Carbomer | 0.05 | | | | 0.1 |
| D | Sodium Hydroxide | 0.02 | | | | 0.04 |
| E | Bisabolol | 0.5 | 0.3 | 0.20 | 0.35 | 1.0 |
|  | Phenoxyethanol, Paraben mixture | 1.00 | 0.60 | 0.70 | 0.60 | 0.5 |
|  | Parfum | 0.05 | 0.10 | 0.10 | 0.05 | 0.05 |

Preparation:
Heat phases A and B separately to ca. 80° C. Stir phase C into phase B and then stir phase A into phase B/C and briefly homogenize.

Add phase D (if required) and cool with stirring to ca. 40° C., add components of phase E in succession to the emulsion and cool to room temperature with stirring. Briefly homogenize.

Instead of the O/W emulsion comprising polymer A.1, also O/W emulsions comprising one or more of the polymers A.2, A.3, A.4, A.5, A.6 or A.7 are prepared.

Hydrodispersion

| Phase | Ingredient/INCI | F.4.1 | F.4.2 | F.4.3 | F.4.4 | F.4.5 |
|---|---|---|---|---|---|---|
| A | Stearyl Alcohol | 0.5 | 1.5 | | | 2.0 |
|  | Cetyl Alcohol | | | 1.00 | 2.5 | |
|  | C12-15 Alkyl Benzoate | | 2.5 | | 4.0 | |
|  | Dicapryl Ether | | 4.0 | | | 6.0 |
|  | Butylene glycol | 4.0 | | 2.0 | 1.0 | |
|  | Dicaprylate/Dicaprate | | | | | |
|  | Dicapryl Carbonate | | 2.0 | 3.0 | | 4.0 |
|  | Cyclopentasiloxane, Cyclohexasiloxane | | | | 2.0 | 0.5 |
|  | Simmondsia Chinensis (Jojoba) Seed Oil | 2.0 | | 0.5 | | |
|  | Shea Butter | | 2.0 | | 1.0 | |
|  | Hydrogenated Polyisobutene | 3.0 | 1.0 | 7.0 | 0.5 | 2.0 |
|  | Squalane | | | | 2.0 | 0.5 |
|  | Vitamin E Acetate | 0.50 | | 0.25 | | 1.00 |
| B | Acrylate/C10-30 Alkyl Acrylate Crosspolymer | 0.3 | 0.1 | 0.2 | 0.15 | 0.2 |
| C | Aqua | ad 100 | ad 100 | ad 100 | ad 100 | ad 100 |
|  | Polyacrylamide, C13-14 Isoparaffin, Laureth-7 | | 1.0 | 1.5 | 0.75 | |
|  | Polymer A.1 | 2.5 | 2.0 | 0.9 | 1.5 | 3.0 |
|  | Propylene Glycol | 3.00 | 5.0 | 2.5 | 7.50 | 10.0 |
| D | Sodium Hydroxide | 0.12 | 0.04 | 0.08 | 0.06 | 0.08 |
| E | Niacinamide | 0.30 | 3.0 | 1.5 | 0.5 | 0.20 |
|  | Aqua | 2.0 | 10.0 | 5.0 | 2.0 | 2.0 |
| F | DMDM Hydantoin | | 0.60 | 0.45 | 0.25 | |
|  | Methylparaben | 0.50 | | 0.25 | 0.15 | |
|  | Phenoxyethanol | 0.50 | 0.40 | | 1.00 | |
|  | Ethylhexylglycerin | | | 1.00 | | 0.80 |
|  | Ethanol | 3.00 | 2.00 | 1.50 | | 7.00 |
| G | fragrance | 0.20 | | 0.05 | | 0.40 |

Preparation:

Heat phases A and C separately to ca. 80° C.

Stir phase B into phase A and then phase C into phase A/B. Briefly homogenize. Add phase D and cool to ca. 40° C. with stirring. Add phase E and cool to ca. 30° C. with stirring. Add phase F and G to the emulsion and cool to room temperature with stirring. Briefly homogenize.

Instead of the hydrodispersion comprising polymer A.1, also hydrodispersions comprising one or more of the polymers A.2, A.3, A.4, A.5, A.6 or A.7 are prepared.

| | | Solids-stabilized emulsion | | | | |
|---|---|---|---|---|---|---|
| Phase | Ingredient/INCI | F.5.1 | F.5.2 | F.5.3 | F.5.4 | F.5.5 |
| A | Mineral Oil | 4.0 | 6.0 | 16.0 | 10.0 | 6.0 |
| | Octyldodecanol | 9.0 | 9.0 | 5.0 | | |
| | Ethylhexyl Isononanoate | 9.0 | 9.0 | 6.0 | 5.0 | 8.0 |
| | Isohexadecane | 9.0 | 5.0 | | 4.0 | 8.0 |
| | Dimethicone | 0.5 | 2.0 | 1.0 | | 1.5 |
| | Cera Microcristallina, Paraffinum Liquidum | | 0.35 | | 0.75 | 3.0 |
| | Phenyl trimethicone | 2.0 | | 1.0 | 2.5 | 3.0 |
| | Silica | 2.5 | | | 6.0 | 2.5 |
| | Aluminum Starch Octenylsuccinate | 2.0 | 1.0 | 0.5 | | |
| | Tapioca Starch | | 0.5 | | | |
| B | Titanium dioxide, coated | 1.0 | 0.5 | 3.0 | 2.0 | 4.0 |
| | Zinc oxide | 5.0 | 10.0 | 2.0 | 3.0 | |
| C | Ammonium Acryloyldimethyltaurate/ Beheneth-25 Methacrylate Crosspolymer | 0.2 | | 1.0 | 0.5 | |
| D | Aqua | ad 100 | ad 100 | ad 100 | ad 100 | ad 100 |
| | Hydroxypropyl Methylcellulose | | | 0.1 | | 0.05 |
| | Sorbitol | 5.0 | 7.0 | 8.5 | 3.0 | 4.5 |
| | Polymer A.1 | 3.0 | 5.0 | 0.9 | 1.4 | 2.0 |
| E | Mixed parabens | 0.3 | 0.6 | 0.2 | | 0.4 |
| | Phenoxyethanol | 0.2 | 0.3 | 0.4 | 0.5 | 0.4 |
| | Diazolidinyl Urea | | | 0.23 | 0.2 | |
| F | Parfum | 0.2 | | 0.3 | 0.1 | |

Preparation:

Heat phase A to 80° C. Add phase B to phase A and homogenize for 3 min. Stir in phase C.

Allow cellulose (if required) to preswell in water, then add the remaining ingredients of phase D and heat to 80° C.

Stir phase D into phase A+B+C and homogenize. Cool emulsion to ca. 40° C. with stirring and add phase E and F. Cool to RT with stirring and homogenize.

Instead of the solids-stabilized emulsion comprising polymer A.1, also solids-stabilized emulsions comprising one or more of the polymers A.2, A.3, A.4, A.5, A.6 or A.7 are prepared.

| | | Sunscreen cream | | | | |
|---|---|---|---|---|---|---|
| Phase | Ingredient/INCI | F.6.1 | F.6.2 | F.6.3 | F.6.4 | F.6.5 |
| A | Aqua | ad 100 | ad 100 | ad 100 | ad 100 | ad 100 |
| | Disodium EDTA | 0.1 | 0.1 | 0.1 | 0.1 | 0.1 |
| | Butylene Glycol | 3.00 | 7.50 | 8.0 | 7.50 | 5.00 |
| | Benzophenone-4 | 2.0 | | | 4.0 | |
| | Phenylbenzimidazole Sulfonic acid | | 0.50 | 4.00 | | 8.0 |
| | Triethanolamine | 1.0 | 0.25 | 2.0 | 2.0 | 4.0 |
| | Panthenol | 0.5 | | 0.75 | | 1.0 |
| | Polymer A.1 | 2.5 g | 0.5 g | 2.0 g | 4.0 | 1.5 |
| | Xanthan gum | | 0.3 | 0.15 | | 0.2 |
| B | Octocrylene | 8.0 | | | 7.5 | |
| | Ethylhexyl Methoxycinnamate, Diethylamino Hydroxybenzoyl Hexyl Benzoate | 5.0 | 10.0 | 8.0 | 3.0 | 7.0 |
| | Steareth-21 | 2.0 | 3.0 | | 2.5 | |
| | Steareth-2 | 1.5 | | | | |
| | PEG-40 Stearate | | | 1.0 | | 2.0 |
| | Glycerin monostearate SE | | 1.0 | 3.0 | 1.5 | 1.5 |
| | Dibutyl Adipate | 3.0 | 5.0 | 3.5 | 2.5 | 2.0 |
| | Cetearyl Alcohol | 2.0 | | | 0.5 | 3.0 |

Sunscreen cream

| Phase | Ingredient/INCI | F.6.1 | F.6.2 | F.6.3 | F.6.4 | F.6.5 |
|---|---|---|---|---|---|---|
| | Stearyl Alcohol | 1.5 | 3.0 | 2.5 | 0.6 | 2.0 |
| | *Butyrospermum Parkii* (Shea Butter) | 1.0 | 0.5 | | 1.0 | 1.5 |
| | Dimethicone | 1.0 | 0.5 | 1.5 | 0.8 | 2.0 |
| | PVP Hexadecene Copolymer | 0.20 | | 0.50 | 0.8 | 1.00 |
| | Bisabolol | 0.2 | 0.1 | | | 0.3 |
| C | DMDM Hydantoin | 0.5 | 0.5 | 0.5 | 0.5 | 0.75 |
| | Water, *Aloe Barbadensis* Leaf Juice | | | 0.5 | 1.0 | |
| | Tocopheryl Acetate | 0.60 | 0.5 | 0.4 | 0.25 | 0.3 |
| | Parfum | 0.10 | 0.25 | 0.30 | 0.40 | 0.20 |

Preparation:
Heat phases A and B separately to ca. 80° C.
Stir phase A into phase B and briefly homogenize.
Cool to ca. 40° C. with stirring. Add components of phase C in succession to the emulsion and cool to room temperature with stirring. Briefly homogenize.

Instead of the sunscreen cream comprising polymer A.1, also sunscreen creams comprising one or more of the polymers A.2, A.3, A.4, A.5, A.6 or A.7 are prepared.

Silicone emulsion

| Phase | Ingredient/INCI | F.7.1 | F.7.2 | F.7.3 | F.7.4 | F.7.5 |
|---|---|---|---|---|---|---|
| A | Water | ad 100 | ad 100 | ad 100 | ad 100 | ad 100 |
| | Butylene Glycol | 6.0 | 3.0 | 2.0 | 8.0 | 5.0 |
| | Polymer A.1 | 3.5 | 1.0 | 0.5 | 5.0 | 2.0 |
| | Xanthan Gum | | | 0.1 | | 0.15 |
| | Imidazolidinyl Urea | 0.3 | | 0.2 | | |
| B | Cetyl PEG/PPG-10/1 Dimethicone | 2.5 | 3.5 | 0.5 | 2.0 | 2.5 |
| | PEG-9 Dimethicone | 1.0 | 1.5 | 2.0 | 0.5 | |
| | PEG-14 Dimethicone | | 0.5 | 2.0 | | 2.5 |
| | PEG-11 Methyl Ether Dimethicone | 1.5 | 3.0 | 0.8 | 0.5 | |
| | Polyglyceryl-3 Disiloxane Dimethicone | 1.0 | 2.0 | 0.5 | | |
| | Cyclopentasiloxane, Caprylyl Dimethicone Ethoxy Glucoside | | 0.5 | 5.0 | 2.5 | 3.5 |
| | Phenyl Trimethicone | 5.0 | 3.0 | 1.5 | 7.5 | |
| | Polymethylsilsesquioxane | 2.0 | 1.5 | 1.0 | 0.5 | |
| | Cyclopentasiloxane, Cyclohexasiloxane | 5.0 | 3.0 | 8.0 | | 10.0 |
| | Cetyl Dimethicone | 1.5 | 1.0 | 2.5 | 3.0 | 4.0 |
| | Paraben mixture | 0.2 | 0.2 | 0.2 | 0.2 | 0.2 |
| C | Sodium Citrate | 0.15 | 0.15 | 0.15 | 0.15 | 0.15 |
| | Monosodium Citrate | 0.05 | 0.05 | 0.05 | 0.05 | 0.05 |
| D | Bisabolol | 0.2 | 0.5 | 0.15 | 0.3 | 0.1 |
| | Fragrance | 0.1 | 0.05 | 0.05 | 0.1 | 0.15 |

Preparation
Heat phases A and B separately to ca. 80° C.
Stir phase A into phase B and homogenize.
Stir phase C into phase A+B and homogenize.
Cool to ca. 40° C. with stirring. Add phase C and cool to ca. 30° C. with stirring. Add phase D. Cool to room temperature with stirring and briefly homogenize.

Instead of the silicon emulsion comprising polymer A.1, also silicone emulsions comprising one or more of the polymers A.2, A.3, A.4, A.5, A.6 or A.7 are prepared.

Hydroxycarboxylic acid cream

| Phase | Ingredient/INCI | F.8.1 | F.8.2 | F.8.3 |
|---|---|---|---|---|
| A | Ceteareth-6, Stearyl Alcohol | 2.0 | | 2.5 |
| | Ceteareth-25 | 2.0 | | 2.5 |
| | PEG-100 Stearate, Glyceryl Stearate | | 3.5 | 0.5 |
| | Polyglyceryl-3 Distearate | | 2.0 | |
| | Mineral Oil | 8.0 | 3.5 | 5.0 |
| | Cetearyl Ethylhexanoate | 7.0 | 5.5 | 4.0 |
| | Sorbitan Stearate | 0.5 | 1.5 | 0.5 |
| | Cera Alba | | 0.5 | 1.0 |

Hydroxycarboxylic acid cream

| Phase | Ingredient/INCI | F.8.1 | F.8.2 | F.8.3 |
|---|---|---|---|---|
| | Cetyl Alcohol | 1.5 | 3.5 | 4.0 |
| | Dimethicone | 0.2 | 2.0 | 0.5 |
| B | Panthenol | 1.0 | 0.5 | 0.3 |
| | Propylene Glycol | 3.0 | 2.0 | 5.0 |
| | Polymer A.1 | 1.0 | 3.0 | 5.0 |
| | Hydroxy acid | 3.0 | 7.0 | 10.0 |
| | Aqua | ad 100 | ad 100 | ad 100 |
| C | Sodium Hydroxide | q.s. | q.s. | q.s. |
| D | Bisabolol | 0.2 | 0.1 | 0.3 |
| | preservative | q.s. | q.s. | q.s. |
| | Fragrance | q.s. | q.s. | q.s. |

Note
Alpha-hydroxy acids: lactic acid, citric acid, malic acid, glycolic acid
Dihydroxy acid: tartaric acid
Beta-Hydroxy acid: salicylic acid Adjust pH>3

Preparation

Heat phases A and B separately to ca. 80° C. Optionally adjust pH of phase B to >3 using NaOH. Stir phase B into phase A, briefly homogenize.

Cool to ca. 40° C. with stirring, add components of phase D in succession, homogenize again.

Instead of the hydroxycarboxylic acid cream comprising polymer A.1, also hydroxycarboxylic acid creams comprising one or more of the polymers A.2, A.3, A.4, A.5, A.6 or A.7 are prepared.

Emulsion with deodorant active ingredient

| Phase | Ingredient/INCI | F.9.1 | F.9.2 | F.9.3 | F.9.4 | F.9.5 |
|---|---|---|---|---|---|---|
| | Ceteareth-6, Stearyl Alcohol | 1.5 | 2.0 | | | 1.0 |
| | Ceteareth-25 | 1.5 | 0.5 | | | 1.0 |
| | PEG-40 Hydrogenated Castor Oil | 0.5 | 1.0 | 2.0 | | |
| | Glyceryl Stearate | | 0.5 | 2.0 | 1.0 | |
| | Cetyl Alcohol | 2.0 | 1.0 | 0.5 | 2.5 | 0.2 |
| | Hydrogenated Coco-Glycerides | 2.0 | | | 1.0 | 0.5 |
| | Hydrogenated Polyisobutene | | 10.0 | 20.0 | 5.0 | 3.0 |
| | Decyl Oleate | 3.0 | 2.0 | | 8.0 | 5.0 |
| | Bis-PEG/PPG-14/14 Dimethicone, Cyclopentasiloxane | 3.0 | 3.5 | 4.0 | 2.0 | 1.5 |
| | Talc | 3.0 | 2.5 | | | 1.5 |
| | Magnesium Aluminum Silicate | 1.0 | | 0.5 | 1.0 | 1.5 |
| B | Propylene Glycol | 10.0 | 5.0 | 7.5 | 20.0 | 15.0 |
| | Polymer A.1 | 0.5 | 1.0 | 3.0 | 3.5 | 2.0 |
| | Xanthan gum | 0.2 | 0.1 | | | 0.05 |
| | Cetyl Hydroxyethylcellulose | 0.3 | | | 0.1 | |
| | Aluminum Chlorohydrate | 5.0 | 10.0 | 20.0 | | |
| | Aluminum Zirconium Tetrachlorohydrex GLY | | 15.0 | | 50.0 | 20.0 |
| | Aqua | ad 100 | ad 100 | ad 100 | ad 100 | ad 100 |
| C | Neutralizing agent | q.s. | q.s. | q.s. | q.s. | q.s. |
| D | Alcohol | 5.0 | 10.0 | 25.0 | 7.5 | 6.0 |
| | Allantoin | 0.1 | 0.1 | 0.1 | 0.1 | 0.1 |
| | preservative | q.s. | q.s. | q.s. | q.s. | q.s. |
| | fragrance | q.s. | q.s. | q.s. | q.s. | q.s. |

Preparation

Heat phases A and B to ca. 80° C.

Stir phase B into phase A with homogenization. Optionally adjust to pH 4-5 using phase C. Cool to ca. 40° C., add phase D and leave to cool to room temperature with stirring. Briefly homogenize.

Note: adjust pH of the emulsion to 4-5

Instead of the emulsion with deodorant active ingredient comprising polymer A.1, also emulsions with deodorant active ingredient comprising one or more of the polymers A.2, A.3, A.4, A.5, A.6 or A.7 were prepared.

Hair removal cream

| Phase | Ingredient/INCI | F.10.1 | F.10.2 | F.10.3 |
|---|---|---|---|---|
| A | Glyceryl Stearate | 1.0 | | |
| | Ceteareth-12 | | 1.0 | 2.0 |
| | Ceteareth-20 | | 1.0 | 2.0 |
| | Stearyl Alcohol | | 4.0 | 1.0 |
| | Cetyl Alcohol | 4.0 | | 1.0 |
| | Mineral Oil | | 6.0 | 4.0 |
| | Prunus Armeniaca (Apricot) Kernel Oil | 3.0 | 1.0 | 2.0 |
| B | Propylene Glycol | 1.0 | 2.0 | 10.0 |
| | Calcium Carbonate | 10.0 | | |
| | Calcium Hydroxide | 7.0 | | |
| | Sodium Hydroxide | | 0.4 | 0.6 |
| | Calcium Thioglycolate | 5.0 | 3.0 | 5.0 |
| | Polymer A.1 | 3.0 | 1.5 | 2.0 |
| | Aqua | ad 100 | ad 100 | ad 100 |

Hair removal cream (continued)

| Phase | Ingredient/INCI | F.10.1 | F.10.2 | F.10.3 |
|---|---|---|---|---|
| C | Tocopherol | 0.1 | 0.2 | 0.15 |
|   | Bisabolol | 0.2 | 0.1 | 0.3 |
|   | Fragrance | q.s. | q.s. | q.s. |

Preparation

Heat phase A and B separately to ca. 80° C.

Stir phase B into phase A with homogenization, briefly homogenize.

Cool to ca. 40° C., add phase C, cool to RT with stirring and homogenize again.

Note: adjust pH of the emulsion to >10

Instead of the hair removal cream comprising polymer A.1, also hair removal creams comprising one or more of the polymers A.2, A.3, A.4, A.5, A.6 or A.7 are prepared.

Conditioner Shampoo

| Ingredient/INCI | F.11.1 | F.11.2 | F.11.3 | F.11.4 |
|---|---|---|---|---|
| Aqua | ad 100 | ad 100 | ad 100 | ad 100 |
| Sodium Laureth Sulfate | 35.7 |  | 30.0 | 12.0 |
| Cocamidopropyl Betaine | 13.5 | 15.0 |  |  |
| Disodium Cocoamphodiacetate |  | 10.0 |  |  |
| Sodium Cocoamphoacetate |  |  | 6.0 |  |
| Polysorbate 20 |  | 5.0 |  |  |
| Decyl Glucoside |  | 5.0 |  | 1.5 |
| Laureth-3 |  | 2.0 |  |  |
| Sodium Laureth Sulfate, Glycol Distearate, Cocamide MEA, Laureth-10 |  |  | 3.0 | 2.0 |
| Coco-Glucoside, Glyceryl Oleate |  |  |  | 5.0 |
| Dimethicone |  |  | 2.0 |  |
| Conditioning polymer | 2.0 | 0.5 | 0.75 | 0.4 |
| Polymer A.1 | 0.75 | 1.2 | 0.5 | 1.0 |
| PEG-150 Distearate |  | 3.0 |  |  |
| Citric Acid |  | q.s. | q.s. |  |
| Preservative | q.s. | q.s. | q.s. | q.s. |
| fragrance | q.s. | q.s. | q.s. | q.s. |
| dye | q.s. | q.s. | q.s. | q.s. |
| Sodium Chloride |  |  | 1.0 | 1.0 |

Conditioning polymer is understood as meaning Polyquaternium-7, PQ-10, PQ-16, PQ-39, PQ-44, PQ-46, PQ-67, Guar Hydroxypropyltrimonium Chloride, PQ-87, and combinations of these.

Instead of the conditioner shampoo comprising polymer A.1, also conditioner shampoos comprising one or more of the polymers A.2, A.3, A.4, A.5, A.6 or A.7 are prepared.

Hair Conditioner

| Phase | Ingredient/INCI | F.12.1 | F.12.2 | F.12.3 | F.12.4 | F.12.5 |
|---|---|---|---|---|---|---|
| A | Water | ad 100 | ad 100 | ad 100 | ad 100 | ad 100 |
|   | Polymer A.1 | 2.5 | 1.5 | 3.0 | 0.6 | 2.0 |
|   | Hydroxyethylcellulose | 0.05 | 0.1 |  | 0.2 |  |
|   | Propylene Glycol | 1.0 | 2.0 |  | 0.8 | 0.5 |
|   | Panthenol | 0.5 |  | 0.75 | 0.25 | 0.3 |
| B | Quaternium-91, Cetearyl Alcohol, Cetrimonium Methosulfate | 2.0 |  |  |  | 1.5 |
|   | Distearoyethyl Hydroxyethylmonium Methosulfate, Cetearyl Alcohol |  |  | 3.0 | 4.0 |  |
|   | Hydrogenated Polyisobutene | 1.0 | 1.5 |  | 1.0 |  |
|   | Cyclopentasiloxane |  |  | 2.0 | 1.0 | 0.5 |
|   | Isopropylpalmitate |  | 1.0 |  | 2.0 |  |
|   | Persea Gratissima (Avocado) Oil |  |  |  |  | 2.5 |
|   | Steareth-2 | 0.75 |  | 0.5 |  |  |
|   | Ceteareth-6, Stearyl Alcohol |  | 1.5 |  |  | 0.5 |
|   | Ceteareth-25 |  | 1.5 |  |  |  |
|   | Cetearyl Alcohol | 2.0 | 1.5 | 0.5 | 4.0 |  |
| C | Acrylate/C10-30 Alkyl acrylate-Copolymer | 0.1 |  |  | 0.2 | 0.15 |
| D | Cetrimonium Chloride | 1.5 |  | 3.0 |  |  |
|   | Conditioning Polymer | 2.0 | 6.0 | 3.0 | 1.5 | 0.8 |
| E | Preservative | q.s. | q.s. | q.s. | q.s. | q.s. |
|   | Fragrance | q.s. | q.s. | q.s. | q.s. | q.s. |

Conditioning polymer is understood as meaning Polyquaternium-7, PQ-10, PQ-16, PQ-39, PQ-44, PQ-46, PQ-67, Guar Hydroxypropyltrimonium Chloride, PQ-87, and combinations of these.

Preparation

Heat phases A and B separately to ca. 80° C.

Stir phase C into phase B, then stir phase A into phase B/C and briefly homogenize.

Cool to ca. 50° C. with stirring, add components of phase D in succession and cool to ca. 30° C. with stirring. Add components of phase E in succession and cool to RT with stirring. Briefly homogenize.

Instead of the hair conditioner comprising polymer A.1, also hair conditioners comprising one or more of the polymers A.2, A.3, A.4, A.5, A.6 or A.7 are prepared.

One skilled in the art will recognize that various modifications and variations can be made to the present invention without departing from the spirit or scope of the invention. It is also noted that these materials can be synthesized using a range of temperatures and reaction times. Thus, it is intended that the present invention cover modifications and variations of this invention provided they come within the scope of the appended claims and their equivalents.

What is claimed is:

1. A polymer comprising, in polymerized-in form,
a) at least one polyisocyanate;
b) at least one alcohol of the general formula I

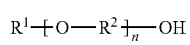
(I)

where
R$^1$ is selected from C$_6$-C$_{40}$-alkyl, C$_6$-C$_{40}$-alkenyl, C$_3$-C$_{10}$-cycloalkyl, C$_6$-C$_{30}$-aryl, C$_7$-C$_{40}$-arylalkyl,
R$^2$ is selected from C$_2$-C$_{10}$-alkylene, C$_6$-C$_{10}$-arylene, C$_7$-C$_{10}$-arylalkylene, n 0 to 200;
c) at least one dendritic polyetherpolyol;
d) optionally at least one compound, different from b) and c), with a molecular weight of at least 300 g/mol, comprising i. at least two OH groups and
ii. at least two groups selected from ether groups and ester groups; and
e) optionally further compounds with in the region of 1 to 9 groups reactive toward isocyanate groups per molecule,
wherein c) is obtained by condensation of at least one tri- or higher-functional alcohol and optionally further di- and/or monofunctional alcohols and/or modifying reagents with the help of an acidic catalyst, and wherein 75 to 95% of OH groups present in c) prior to polymerization are also present as OH groups after polymerization.

2. The polymer according to claim 1, wherein c) is the condensation product of on average at least 3 di-, tri- or higher-functional alcohols.

3. The polymer according to claim 1, wherein c) has a number-average molecular weight M$_n$ of at least 300 g/mol.

4. The polymer according to claim 1, wherein c) comprises polyglycerol.

5. The polymer according to claim 1, wherein the polymer is water-soluble or water-dispersible.

6. The polymer according to claim 1, wherein in the region of 5 to 95% of the OH groups present in c) before the polymerization are also present as OH groups after the polymerization.

7. The polymer according to claim 1, wherein b) comprises a C$_{12}$-C$_{30}$-alcohol which has been ethoxylated with 3 to 100 mol of ethylene oxide per mole.

8. The polymer according to claim 1, wherein d) comprises a polyethylene glycol with a molecular weight M$_n$ in the range from 1500 to 12,000 g/mol.

9. The polymer according to claim 4, wherein the polymer is water-soluble or water-dispersible.

10. The polymer according to claim 9, wherein b) comprises a C$_{12}$-C$_{30}$-alcohol which has been ethoxylated with 3 to 100 mol of ethylene oxide per mole.

11. The polymer according to claim 9, wherein d) comprises a polyethylene glycol with a molecular weight M$_n$ in the range from 1500 to 12,000 g/mol.

* * * * *